United States Patent
Stefanov

(10) Patent No.: US 12,011,186 B2
(45) Date of Patent: Jun. 18, 2024

(54) BEVEL TIP EXPANDABLE MOUTH CATHETER WITH REINFORCING RING

(71) Applicant: Neuravi Limited, Galway (IE)

(72) Inventor: Petrica Stefanov, Loughrea (IE)

(73) Assignee: NEURAVI LIMITED, Galway (IE)

(*) Notice: Subject to any disclaimer, the term of this patent is extended or adjusted under 35 U.S.C. 154(b) by 0 days.

(21) Appl. No.: 17/513,347

(22) Filed: Oct. 28, 2021

(65) Prior Publication Data

US 2023/0132996 A1     May 4, 2023

(51) Int. Cl.
| | |
|---|---|
| *A61B 17/221* | (2006.01) |
| *A61B 17/00* | (2006.01) |
| *A61B 90/00* | (2016.01) |

(52) U.S. Cl.
CPC .. *A61B 17/221* (2013.01); *A61B 2017/00292* (2013.01); *A61B 2017/00867* (2013.01); *A61B 2017/2212* (2013.01); *A61B 2090/3966* (2016.02)

(58) Field of Classification Search
CPC .......... A61B 17/221; A61B 2017/2215; A61B 2017/2212; A61B 17/32056
See application file for complete search history.

(56) References Cited

U.S. PATENT DOCUMENTS

| | | |
|---|---|---|
| 4,243,040 A | 1/1981 | Beecher |
| 4,324,262 A | 4/1982 | Hall |
| 4,351,342 A | 9/1982 | Wiita et al. |
| 4,575,371 A | 3/1986 | Nordqvist et al. |
| 4,592,356 A | 6/1986 | Gutierrez |
| 4,719,924 A | 1/1988 | Crittenden et al. |
| 4,738,666 A | 4/1988 | Fuqua |
| 4,767,404 A | 8/1988 | Renton |
| 4,793,348 A | 12/1988 | Palmaz |

(Continued)

FOREIGN PATENT DOCUMENTS

| | | |
|---|---|---|
| AU | 2015271876 B2 | 9/2017 |
| CN | 1658920 A | 8/2005 |

(Continued)

OTHER PUBLICATIONS

US 6,348,062 B1, 02/2002, Hopkins (withdrawn)

(Continued)

*Primary Examiner* — Shaun L David
(74) *Attorney, Agent, or Firm* — TROUTMAN PEPPER HAMILTON SANDERS LLP

(57) ABSTRACT

The designs and methods disclosed herein are for a clot retrieval catheter with a large bore shaft and a distal braid-supported tip that is expandable to a diameter larger than the outer sheath through which it is delivered. The distal mouth of the tip can be beveled at an angle inclined from the longitudinal axis of the shaft. The braided tip can be braced with a reinforcing ring which can be welded or overmolded to the distal end of the braid and prevents the tip from collapsing under aspiration forces. The reinforcing ring can have relief features positioned to allow the oblique orientation of the ring to maintain a circular inner channel when the tip is compressed and delivered through a guide sheath and expanded at a target site. The distal tip can be expanded to a profile that is either symmetric or asymmetric with the catheter shaft.

20 Claims, 11 Drawing Sheets

(56) References Cited

U.S. PATENT DOCUMENTS

| | | |
|---|---|---|
| 4,873,978 A | 10/1989 | Ginsburg |
| 5,011,488 A | 4/1991 | Ginsburg |
| 5,092,839 A | 3/1992 | Kipperman |
| 5,102,415 A | 4/1992 | Guenther et al. |
| 5,106,364 A | 4/1992 | Hayafuji et al. |
| 5,122,136 A | 6/1992 | Guglielmi et al. |
| 5,123,840 A | 6/1992 | Nates |
| 5,171,233 A | 12/1992 | Amplatz |
| 5,234,437 A | 8/1993 | Sepetka |
| 5,256,144 A | 10/1993 | Kraus et al. |
| 5,261,916 A | 11/1993 | Engelson |
| 5,372,124 A | 12/1994 | Takayama et al. |
| 5,385,562 A | 1/1995 | Adams |
| 5,387,219 A | 2/1995 | Rappe |
| 5,387,226 A | 2/1995 | Miraki |
| 5,396,902 A | 3/1995 | Brennen et al. |
| 5,449,372 A | 9/1995 | Schmaltz |
| 5,520,651 A | 5/1996 | Sutcu |
| 5,538,008 A | 7/1996 | Crowe |
| 5,538,512 A | 7/1996 | Zenzon et al. |
| 5,549,626 A | 8/1996 | Miller et al. |
| 5,558,652 A | 9/1996 | Henke |
| 5,601,600 A | 2/1997 | Ton |
| 5,609,627 A | 3/1997 | Goicoechea et al. |
| 5,624,461 A | 4/1997 | Mariant |
| 5,639,277 A | 6/1997 | Mariant |
| 5,645,558 A | 7/1997 | Horton |
| 5,658,296 A | 8/1997 | Bates |
| 5,662,671 A | 9/1997 | Barbut |
| 5,695,519 A | 12/1997 | Summers et al. |
| 5,709,704 A | 1/1998 | Nott et al. |
| 5,713,853 A | 2/1998 | Clark |
| 5,728,078 A | 3/1998 | Powers, Jr. |
| 5,769,871 A | 6/1998 | Mers Kelly |
| 5,779,716 A | 7/1998 | Cano |
| 5,810,874 A | 9/1998 | Lefebvre |
| 5,814,064 A | 9/1998 | Daniel et al. |
| 5,827,304 A | 10/1998 | Hart |
| 5,846,248 A | 12/1998 | Chu et al. |
| 5,846,251 A | 12/1998 | Hart |
| 5,855,598 A | 1/1999 | Pinchuk |
| 5,893,869 A | 4/1999 | Barnhart et al. |
| 5,895,398 A | 4/1999 | Wensel |
| 5,897,567 A | 4/1999 | Ressemann |
| 5,904,698 A | 5/1999 | Thomas et al. |
| 5,911,725 A | 6/1999 | Boury |
| 5,935,139 A | 8/1999 | Bates |
| 5,938,645 A | 8/1999 | Gordon |
| 5,947,995 A | 9/1999 | Samuels |
| 5,968,057 A | 10/1999 | Taheri |
| 5,971,938 A | 10/1999 | Hart et al. |
| 5,997,939 A | 12/1999 | Moechnig et al. |
| 6,022,343 A | 2/2000 | Johnson et al. |
| 6,063,113 A | 5/2000 | Kavteladze |
| 6,066,149 A | 5/2000 | Samson et al. |
| 6,066,158 A | 5/2000 | Engelson |
| 6,093,196 A | 7/2000 | Okada |
| 6,093,199 A | 7/2000 | Brown et al. |
| 6,096,053 A | 8/2000 | Bates |
| 6,099,534 A | 8/2000 | Bates |
| 6,102,932 A | 8/2000 | Kurz |
| 6,106,548 A | 8/2000 | Roubin et al. |
| 6,129,739 A | 10/2000 | Khosravi |
| 6,142,957 A | 11/2000 | Diamond et al. |
| 6,146,396 A | 11/2000 | Kónya et al. |
| 6,146,404 A | 11/2000 | Kim |
| 6,165,194 A | 12/2000 | Denardo |
| 6,165,199 A | 12/2000 | Barbut |
| 6,168,604 B1 | 1/2001 | Cano |
| 6,168,622 B1 | 1/2001 | Mazzocchi |
| 6,174,318 B1 | 1/2001 | Bates et al. |
| 6,179,861 B1 | 1/2001 | Khosravi |
| 6,203,561 B1 | 3/2001 | Ramee |
| 6,214,026 B1 | 4/2001 | Lepak |
| 6,221,006 B1 | 4/2001 | Dubrul |
| 6,238,412 B1 | 5/2001 | Dubrul |
| 6,245,087 B1 | 6/2001 | Addis |
| 6,251,122 B1 | 6/2001 | Tsukernik |
| 6,254,571 B1 | 7/2001 | Hart |
| 6,264,663 B1 | 7/2001 | Cano |
| 6,306,163 B1 | 10/2001 | Fitz |
| 6,309,379 B1 | 10/2001 | Willard |
| 6,312,407 B1 | 11/2001 | Zando-Azizi et al. |
| 6,312,444 B1 | 11/2001 | Barbut |
| 6,315,778 B1 | 11/2001 | Gambale et al. |
| 6,325,819 B1 | 12/2001 | Pavcnik et al. |
| 6,334,864 B1 | 1/2002 | Amplatz et al. |
| 6,336,934 B1 | 1/2002 | Gilson et al. |
| 6,346,116 B1 | 2/2002 | Brooks et al. |
| 6,348,056 B1 | 2/2002 | Bates |
| 6,350,271 B1 | 2/2002 | Kurz et al. |
| 6,361,545 B1 | 3/2002 | Macoviak |
| 6,371,963 B1 | 4/2002 | Nishtala et al. |
| 6,375,668 B1 | 4/2002 | Gifford et al. |
| 6,383,205 B1 | 5/2002 | Samson et al. |
| 6,383,206 B1 | 5/2002 | Gillick |
| 6,391,037 B1 | 5/2002 | Greenhalgh |
| 6,402,771 B1 | 6/2002 | Palmer |
| 6,409,683 B1 | 6/2002 | Fonseca et al. |
| 6,416,541 B2 | 7/2002 | Denardo |
| 6,425,909 B1 | 7/2002 | Dieck et al. |
| 6,432,122 B1 | 8/2002 | Gilson et al. |
| 6,436,112 B2 | 8/2002 | Wensel |
| 6,458,139 B1 | 10/2002 | Palmer |
| 6,485,497 B2 | 11/2002 | Wensel |
| 6,485,501 B1 | 11/2002 | Green |
| 6,485,502 B2 | 11/2002 | Don Michael |
| 6,511,492 B1 | 1/2003 | Rosenbluth |
| 6,517,551 B1 | 2/2003 | Driskill |
| 6,520,934 B1 | 2/2003 | Lee et al. |
| 6,520,951 B1 | 2/2003 | Carrillo, Jr. et al. |
| 6,530,935 B2 | 3/2003 | Wensel |
| 6,530,939 B1 | 3/2003 | Hopkins |
| 6,540,768 B1 | 4/2003 | Diaz et al. |
| 6,544,279 B1 | 4/2003 | Hopkins |
| 6,551,341 B2 | 4/2003 | Boylan et al. |
| 6,551,342 B1 | 4/2003 | Shen et al. |
| 6,575,997 B1 | 6/2003 | Palmer et al. |
| 6,582,448 B1 | 6/2003 | Boyle |
| 6,585,756 B1 | 7/2003 | Strecker |
| 6,589,265 B1 | 7/2003 | Palmer et al. |
| 6,592,607 B1 | 7/2003 | Palmer et al. |
| 6,592,616 B1 | 7/2003 | Stack |
| 6,602,271 B2 | 8/2003 | Adams |
| 6,602,272 B2 | 8/2003 | Boylan et al. |
| 6,605,102 B1 | 8/2003 | Mazzocchi et al. |
| 6,610,077 B1 | 8/2003 | Hancock et al. |
| 6,616,679 B1 | 9/2003 | Khosravi |
| 6,632,241 B1 | 10/2003 | Hancock et al. |
| 6,638,245 B2 | 10/2003 | Miller |
| 6,638,293 B1 | 10/2003 | Makower et al. |
| 6,641,590 B1 | 11/2003 | Palmer et al. |
| 6,652,555 B1 | 11/2003 | VanTassel et al. |
| 6,656,218 B1 | 12/2003 | Denardo et al. |
| 6,660,021 B1 | 12/2003 | Palmer et al. |
| 6,663,650 B2 | 12/2003 | Sepetka |
| 6,673,089 B1 | 1/2004 | Yassour et al. |
| 6,685,722 B1 | 2/2004 | Rosenbluth |
| 6,692,504 B2 | 2/2004 | Kurz et al. |
| 6,692,508 B2 | 2/2004 | Wensel |
| 6,692,509 B2 | 2/2004 | Wensel |
| 6,702,782 B2 | 3/2004 | Miller |
| 6,712,834 B2 | 3/2004 | Yassour et al. |
| 6,726,701 B2 | 4/2004 | Gilson et al. |
| 6,726,703 B2 | 4/2004 | Broome et al. |
| 6,730,104 B1 | 5/2004 | Sepetka |
| 6,824,545 B2 | 11/2004 | Sepetka |
| 6,855,155 B2 | 2/2005 | Denardo et al. |
| 6,878,163 B2 | 4/2005 | Denardo et al. |
| 6,890,340 B2 | 5/2005 | Duane |
| 6,913,612 B2 | 7/2005 | Palmer |
| 6,913,618 B2 | 7/2005 | Denardo et al. |
| 6,953,472 B2 | 10/2005 | Palmer et al. |
| 6,989,019 B2 | 1/2006 | Mazzocchi |

(56) References Cited

U.S. PATENT DOCUMENTS

| | | |
|---|---|---|
| 6,989,021 B2 | 1/2006 | Bosma et al. |
| 6,994,718 B2 | 2/2006 | Groothuis et al. |
| 6,997,939 B2 | 2/2006 | Linder |
| 7,004,954 B1 | 2/2006 | Voss et al. |
| 7,004,955 B2 | 2/2006 | Shen |
| 7,004,956 B2 | 2/2006 | Palmer |
| 7,008,434 B2 | 3/2006 | Kurz et al. |
| 7,033,376 B2 | 4/2006 | Tsukernik |
| 7,041,116 B2 | 5/2006 | Goto |
| 7,048,758 B2 | 5/2006 | Boyle |
| 7,058,456 B2 | 6/2006 | Pierce |
| 7,063,707 B2 | 6/2006 | Bose |
| 7,153,320 B2 | 12/2006 | Euteneuer et al. |
| 7,175,655 B1 | 2/2007 | Malaei |
| 7,179,273 B1 | 2/2007 | Palmer et al. |
| 7,220,269 B1 | 5/2007 | Ansel |
| 7,220,271 B2 | 5/2007 | Clubb |
| 7,226,464 B2 | 6/2007 | Garner et al. |
| 7,229,472 B2 | 6/2007 | DePalma et al. |
| 7,232,462 B2 | 6/2007 | Schaeffer |
| 7,288,112 B2 | 10/2007 | Denardo et al. |
| 7,306,618 B2 | 12/2007 | Demond |
| 7,316,692 B2 | 1/2008 | Huffmaster |
| 7,323,001 B2 | 1/2008 | Cubb |
| 7,331,976 B2 | 2/2008 | McGuckin, Jr. et al. |
| 7,344,550 B2 | 3/2008 | Carrison et al. |
| 7,399,308 B2 | 7/2008 | Borillo et al. |
| 7,410,491 B2 | 8/2008 | Hopkins |
| 7,452,496 B2 | 11/2008 | Brady et al. |
| 7,491,215 B2 | 2/2009 | Vale et al. |
| 7,491,216 B2 | 2/2009 | Brady |
| 7,510,565 B2 | 3/2009 | Gilson et al. |
| 7,534,252 B2 | 5/2009 | Sepetka |
| 7,556,636 B2 | 7/2009 | Mazzocchi |
| 7,582,111 B2 | 9/2009 | Krolik et al. |
| 7,594,926 B2 | 9/2009 | Linder |
| 7,604,649 B2 | 10/2009 | McGuckin et al. |
| 7,618,434 B2 | 11/2009 | Santra et al. |
| 7,662,165 B2 | 2/2010 | Gilson et al. |
| 7,670,356 B2 | 3/2010 | Mazzocchi |
| 7,691,121 B2 | 4/2010 | Rosenbluth |
| 7,691,124 B2 | 4/2010 | Balgobin |
| 7,708,770 B2 | 5/2010 | Linder |
| 7,736,385 B2 | 6/2010 | Agnew |
| 7,766,934 B2 | 8/2010 | Pal |
| 7,771,452 B2 | 8/2010 | Pal |
| 7,780,694 B2 | 8/2010 | Palmer |
| 7,780,696 B2 | 8/2010 | Daniel et al. |
| 7,819,893 B2 | 10/2010 | Brady et al. |
| 7,828,815 B2 | 11/2010 | Mazzocchi |
| 7,846,176 B2 | 11/2010 | Mazzocchi |
| 7,846,175 B2 | 12/2010 | Bonnette et al. |
| 7,850,708 B2 | 12/2010 | Pal |
| 7,887,560 B2 | 2/2011 | Kusleika |
| 7,901,426 B2 | 3/2011 | Gilson et al. |
| 7,914,549 B2 | 3/2011 | Morsi |
| 7,922,732 B2 | 4/2011 | Mazzocchi |
| 7,927,349 B2 | 4/2011 | Brady et al. |
| 7,927,784 B2 | 4/2011 | Simpson |
| 7,931,659 B2 | 4/2011 | Bose et al. |
| 7,998,165 B2 | 8/2011 | Huffmaster |
| 8,002,822 B2 | 8/2011 | Glocker et al. |
| 8,021,379 B2 | 9/2011 | Thompson et al. |
| 8,021,380 B2 | 9/2011 | Thompson et al. |
| 8,043,326 B2 | 10/2011 | Hancock et al. |
| 8,048,151 B2 | 11/2011 | O'Brien et al. |
| 8,052,640 B2 | 11/2011 | Fiorella et al. |
| 8,057,497 B1 | 11/2011 | Raju et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,935 B2 | 1/2012 | Rosenbluth et al. |
| 8,109,941 B2 | 2/2012 | Richardson |
| 8,118,829 B2 | 2/2012 | Carrison et al. |
| 8,123,769 B2 | 2/2012 | Osborne |
| 8,137,377 B2 | 3/2012 | Palmer et al. |
| 8,142,422 B2 | 3/2012 | Makower et al. |
| 8,142,442 B2 | 3/2012 | Palmer et al. |
| 8,182,508 B2 | 5/2012 | Magnuson et al. |
| 8,187,298 B2 | 5/2012 | Pal |
| 8,246,641 B2 | 8/2012 | Osborne et al. |
| 8,246,672 B2 | 8/2012 | Osborne |
| 8,252,017 B2 | 8/2012 | Paul, Jr. et al. |
| 8,252,018 B2 | 8/2012 | Valaie |
| 8,357,178 B2 | 1/2013 | Grandfield et al. |
| 8,357,179 B2 | 1/2013 | Grandfield et al. |
| 8,357,893 B2 | 1/2013 | Xu et al. |
| 8,361,095 B2 | 1/2013 | Osborne |
| 8,366,663 B2 | 2/2013 | Fiorella et al. |
| 8,372,133 B2 | 2/2013 | Douk et al. |
| 8,382,742 B2 | 2/2013 | Hermann et al. |
| 8,409,215 B2 | 4/2013 | Sepetka et al. |
| 8,419,748 B2 | 4/2013 | Valaie |
| 8,460,312 B2 | 6/2013 | Bose et al. |
| 8,460,313 B2 | 6/2013 | Huffmaster |
| 8,486,104 B2 | 7/2013 | Samson et al. |
| 8,529,596 B2 | 9/2013 | Grandfield et al. |
| 8,574,262 B2 | 11/2013 | Ferrera et al. |
| 8,579,915 B2 | 11/2013 | French et al. |
| 8,585,643 B2 | 11/2013 | Vo et al. |
| 8,585,713 B2 | 11/2013 | Ferrera et al. |
| 8,608,761 B2 | 12/2013 | Osbourne et al. |
| 8,679,142 B2 | 3/2014 | Slee et al. |
| 8,696,622 B2 | 4/2014 | Fiorella et al. |
| 8,702,652 B2 | 4/2014 | Fiorella et al. |
| 8,702,724 B2 | 4/2014 | Olsen et al. |
| 8,784,434 B2 | 7/2014 | Rosenbluth et al. |
| 8,784,441 B2 | 7/2014 | Rosenbluth et al. |
| 8,795,305 B2 | 8/2014 | Grandfield et al. |
| 8,795,317 B2 | 8/2014 | Grandfield et al. |
| 8,795,345 B2 | 8/2014 | Grandfield et al. |
| 8,814,892 B2 | 8/2014 | Galdonik et al. |
| 8,814,925 B2 | 8/2014 | Hilaire et al. |
| 8,900,265 B1 | 12/2014 | Ulm, III |
| 8,939,991 B2 | 1/2015 | Krolick et al. |
| 8,945,143 B2 | 2/2015 | Ferrera et al. |
| 8,945,172 B2 | 2/2015 | Ferrera et al. |
| 8,968,330 B2 | 3/2015 | Rosenbluth et al. |
| 9,039,749 B2 | 5/2015 | Shrivastava et al. |
| 9,072,537 B2 | 7/2015 | Grandfield et al. |
| 9,113,936 B2 | 8/2015 | Palmer et al. |
| 9,119,656 B2 | 9/2015 | Bose et al. |
| 9,138,307 B2 | 9/2015 | Valaie |
| 9,149,609 B2 | 10/2015 | Ansel et al. |
| 9,155,552 B2 | 10/2015 | Ulm, III |
| 9,161,766 B2 | 10/2015 | Slee et al. |
| 9,173,668 B2 | 11/2015 | Ulm, III |
| 9,186,487 B2 | 11/2015 | Dubrul et al. |
| 9,198,687 B2 | 12/2015 | Fulkerson et al. |
| 9,204,887 B2 | 12/2015 | Cully et al. |
| 9,221,132 B2 | 12/2015 | Bowman |
| 9,232,992 B2 | 1/2016 | Heidner |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,635 B2 | 5/2017 | Vale et al. |
| 9,642,675 B2 | 5/2017 | Werneth et al. |
| 9,655,633 B2 | 5/2017 | Leynov et al. |
| 9,655,645 B2 | 5/2017 | Staunton |

(56) References Cited

U.S. PATENT DOCUMENTS

| | | |
|---|---|---|
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulacheski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 10,028,759 B2 | 7/2018 | Wallace et al. |
| 10,149,692 B2 | 12/2018 | Turjman et al. |
| 10,172,634 B1 | 1/2019 | Horowitz |
| 10,183,145 B2 | 1/2019 | Yang et al. |
| 10,265,086 B2 | 4/2019 | Vale |
| 10,610,668 B2 | 4/2020 | Burkholz et al. |
| 10,624,659 B2 | 4/2020 | Gamba et al. |
| 10,716,915 B2 | 7/2020 | Ogle et al. |
| 10,835,271 B2 * | 11/2020 | Ma .................. A61B 17/12109 |
| 10,835,272 B2 | 11/2020 | Yang et al. |
| 11,076,876 B2 | 8/2021 | Vale |
| 11,272,945 B2 | 3/2022 | Shrivastava |
| 11,273,062 B2 | 3/2022 | Goldberg et al. |
| 2001/0001315 A1 | 5/2001 | Bates |
| 2001/0011182 A1 | 8/2001 | Dubrul et al. |
| 2001/0016755 A1 | 8/2001 | Addis |
| 2001/0041899 A1 | 11/2001 | Foster |
| 2001/0044598 A1 | 11/2001 | Parodi |
| 2001/0044634 A1 | 11/2001 | Don Michael et al. |
| 2001/0051810 A1 | 12/2001 | Dubrul |
| 2002/0002383 A1 | 1/2002 | Sepetka et al. |
| 2002/0016609 A1 | 2/2002 | Wensel |
| 2002/0022859 A1 | 2/2002 | Hogendijk |
| 2002/0026211 A1 | 2/2002 | Khosravi |
| 2002/0049468 A1 | 4/2002 | Streeter |
| 2002/0052620 A1 | 5/2002 | Barvut |
| 2002/0068954 A1 | 6/2002 | Foster |
| 2002/0072764 A1 | 6/2002 | Sepetka |
| 2002/0082558 A1 | 6/2002 | Samson |
| 2002/0091407 A1 | 7/2002 | Zadno-Azizi et al. |
| 2002/0095171 A1 | 7/2002 | Belef |
| 2002/0123765 A1 | 9/2002 | Sepetka |
| 2002/0143362 A1 | 10/2002 | Macoviak et al. |
| 2002/0156455 A1 | 10/2002 | Barbut |
| 2002/0161393 A1 | 10/2002 | Demond |
| 2002/0165576 A1 | 11/2002 | Boyle et al. |
| 2002/0173819 A1 | 11/2002 | Leeflang et al. |
| 2002/0177800 A1 | 11/2002 | Bagaoisan et al. |
| 2002/0188276 A1 | 12/2002 | Evans |
| 2003/0004536 A1 | 1/2003 | Boylan et al. |
| 2003/0004538 A1 | 1/2003 | Secrest |
| 2003/0004542 A1 | 1/2003 | Wensel |
| 2003/0009146 A1 | 1/2003 | Muni |
| 2003/0009191 A1 | 1/2003 | Wensel |
| 2003/0023204 A1 | 1/2003 | Vo et al. |
| 2003/0040769 A1 | 2/2003 | Kelley et al. |
| 2003/0040772 A1 | 2/2003 | Hyodoh et al. |
| 2003/0050663 A1 | 3/2003 | Khachin |
| 2003/0100847 A1 | 5/2003 | D'Aquanni et al. |
| 2003/0105484 A1 | 6/2003 | Boyle et al. |
| 2003/0125798 A1 | 7/2003 | Matrin |
| 2003/0130682 A1 | 7/2003 | Broome et al. |
| 2003/0144687 A1 | 7/2003 | Brady et al. |
| 2003/0144689 A1 * | 7/2003 | Brady .................. A61F 2/0108 606/200 |
| 2003/0153940 A1 | 8/2003 | Nohilly et al. |
| 2003/0153943 A1 | 8/2003 | Michael et al. |
| 2003/0153944 A1 | 8/2003 | Phung |
| 2003/0163064 A1 | 8/2003 | Vrba |
| 2003/0163158 A1 | 8/2003 | Wlite |
| 2003/0171769 A1 | 9/2003 | Barbu |
| 2003/0176884 A1 | 9/2003 | Berrada et al. |
| 2003/0187495 A1 | 10/2003 | Cully et al. |
| 2003/0195537 A1 | 10/2003 | Dubrul |
| 2003/0195554 A1 | 10/2003 | Shen |
| 2003/0199917 A1 | 10/2003 | Knudson |
| 2003/0204202 A1 | 10/2003 | Palmer |
| 2003/0212430 A1 | 11/2003 | Bose |
| 2003/0216611 A1 | 11/2003 | Q. Vu |
| 2003/0236533 A1 | 12/2003 | Wilson |
| 2004/0010280 A1 | 1/2004 | Adams et al. |
| 2004/0010282 A1 | 1/2004 | Kusleika |
| 2004/0014002 A1 | 1/2004 | Lundgren |
| 2004/0068288 A1 | 4/2004 | Palmer et al. |
| 2004/0073243 A1 | 4/2004 | Sepetka |
| 2004/0079429 A1 | 4/2004 | Miller |
| 2004/0082962 A1 | 4/2004 | Demarais et al. |
| 2004/0093065 A1 | 5/2004 | Yachia et al. |
| 2004/0133231 A1 | 7/2004 | Maitland |
| 2004/0138692 A1 | 7/2004 | Phung |
| 2004/0153049 A1 | 8/2004 | Hewitt et al. |
| 2004/0153118 A1 | 8/2004 | Clubb |
| 2004/0193107 A1 | 9/2004 | Pierpont et al. |
| 2004/0199202 A1 | 10/2004 | Dubrul et al. |
| 2004/0260333 A1 | 12/2004 | Dubrul et al. |
| 2005/0015047 A1 | 1/2005 | Shah |
| 2005/0020974 A1 | 1/2005 | Noriega |
| 2005/0033348 A1 | 2/2005 | Sepetka |
| 2005/0038447 A1 | 2/2005 | Huffmaster |
| 2005/0038468 A1 | 2/2005 | Panetta et al. |
| 2005/0049619 A1 | 3/2005 | Sepetka |
| 2005/0049669 A1 | 3/2005 | Jones |
| 2005/0049670 A1 | 3/2005 | Jones et al. |
| 2005/0055033 A1 | 3/2005 | Leslie et al. |
| 2005/0055047 A1 | 3/2005 | Greenhalgh |
| 2005/0059993 A1 | 3/2005 | Ramzipoor et al. |
| 2005/0059995 A1 | 3/2005 | Sepetka |
| 2005/0085849 A1 | 4/2005 | Sepetka |
| 2005/0090857 A1 | 4/2005 | Kusleika et al. |
| 2005/0119524 A1 | 6/2005 | Sckine et al. |
| 2005/0119668 A1 | 6/2005 | Teague et al. |
| 2005/0125024 A1 | 6/2005 | Sepetka |
| 2005/0131449 A1 * | 6/2005 | Salahieh .................. A61F 2/01 606/200 |
| 2005/0149111 A1 | 7/2005 | Kanazawa et al. |
| 2005/0171566 A1 | 8/2005 | Kanamaru |
| 2005/0187570 A1 | 8/2005 | Nguyen et al. |
| 2005/0267491 A1 | 8/2005 | Kellett et al. |
| 2005/0216030 A1 | 9/2005 | Sepetka |
| 2005/0216050 A1 | 9/2005 | Sepetka |
| 2005/0288686 A1 | 9/2005 | Sepetka |
| 2005/0228417 A1 | 10/2005 | Teitelbaum et al. |
| 2006/0009785 A1 | 1/2006 | Maitland et al. |
| 2006/0009799 A1 | 1/2006 | Kleshinski et al. |
| 2006/0010636 A1 | 1/2006 | Vacher |
| 2006/0030933 A1 | 2/2006 | DeLeggge et al. |
| 2006/0036271 A1 | 2/2006 | Schomer et al. |
| 2006/0058836 A1 | 3/2006 | Bose |
| 2006/0058837 A1 | 3/2006 | Bose |
| 2006/0058838 A1 | 3/2006 | Bose |
| 2006/0064151 A1 | 3/2006 | Guterman et al. |
| 2006/0149313 A1 | 7/2006 | Arguello et al. |

(56) References Cited

U.S. PATENT DOCUMENTS

| | | |
|---|---|---|
| 2006/0155305 A1 | 7/2006 | Freudenthal |
| 2006/0155322 A1 | 7/2006 | Sater et al. |
| 2006/0161187 A1 | 7/2006 | Levine et al. |
| 2006/0195137 A1 | 8/2006 | Sepetka |
| 2006/0224177 A1 | 10/2006 | Finitsis |
| 2006/0224179 A1 | 10/2006 | Kucharczyk |
| 2006/0229638 A1 | 10/2006 | Abrams et al. |
| 2006/0282111 A1 | 12/2006 | Morsi |
| 2006/0287701 A1 | 12/2006 | Pal |
| 2007/0088383 A1 | 4/2007 | Pal et al. |
| 2007/0142858 A1 | 6/2007 | Bates |
| 2007/0149996 A1 | 6/2007 | Coughlin |
| 2007/0156170 A1 | 7/2007 | Hancock |
| 2007/0165170 A1 | 7/2007 | Fukuda |
| 2007/0179513 A1 | 8/2007 | Deutsch |
| 2007/0191866 A1 | 8/2007 | Palmer et al. |
| 2007/0198028 A1 | 8/2007 | Miloslavski |
| 2007/0198051 A1 | 8/2007 | Clubb et al. |
| 2007/0198075 A1 | 8/2007 | Levy |
| 2007/0208367 A1 | 9/2007 | Fiorella |
| 2007/0208371 A1 | 9/2007 | French |
| 2007/0213765 A1 | 9/2007 | Adams et al. |
| 2007/0225749 A1 | 9/2007 | Martin |
| 2007/0239182 A1 | 10/2007 | Glines et al. |
| 2007/0239254 A1 | 10/2007 | Chia et al. |
| 2007/0244505 A1 | 10/2007 | Gilson et al. |
| 2007/0270902 A1 | 11/2007 | Slazas et al. |
| 2007/0288038 A1 | 12/2007 | Bimbo |
| 2007/0293887 A1 | 12/2007 | Okushi et al. |
| 2008/0045881 A1 | 2/2008 | Teitelbaum et al. |
| 2008/0082107 A1 | 4/2008 | Miller et al. |
| 2008/0086190 A1 | 4/2008 | Ta |
| 2008/0091223 A1 | 4/2008 | Pokorney |
| 2008/0097398 A1 | 4/2008 | Mitelberg |
| 2008/0109031 A1 | 5/2008 | Sepetka |
| 2008/0109032 A1 | 5/2008 | Sepetka |
| 2008/0119886 A1 | 5/2008 | Greenhalgh et al. |
| 2008/0177296 A1 | 7/2008 | Sepetka |
| 2008/0183197 A1 | 7/2008 | Sepetka |
| 2008/0183198 A1 | 7/2008 | Sepetka |
| 2008/0183205 A1 | 7/2008 | Sepetka |
| 2008/0188876 A1 | 8/2008 | Sepetka |
| 2008/0188885 A1 | 8/2008 | Sepetka |
| 2008/0188928 A1 | 8/2008 | Salahieh |
| 2008/0200946 A1 | 8/2008 | Braun |
| 2008/0215077 A1 | 9/2008 | Sepetka |
| 2008/0221600 A1 | 9/2008 | Dieck et al. |
| 2008/0228209 A1 | 9/2008 | DeMello et al. |
| 2008/0234706 A1 | 9/2008 | Sepetka |
| 2008/0243170 A1 | 10/2008 | Jenson |
| 2008/0255596 A1 | 10/2008 | Jenson |
| 2008/0262528 A1 | 10/2008 | Martin |
| 2008/0262532 A1 | 10/2008 | Martin |
| 2008/0269774 A1 | 10/2008 | Garcia et al. |
| 2008/0275488 A1 | 11/2008 | Fleming |
| 2008/0275493 A1 | 11/2008 | Farmiga |
| 2008/0281350 A1 | 11/2008 | Sepetka |
| 2008/0312681 A1 | 12/2008 | Ansel |
| 2009/0024157 A1 | 1/2009 | Anukhin |
| 2009/0054918 A1 | 2/2009 | Henson |
| 2009/0069828 A1 | 3/2009 | Martin |
| 2009/0076539 A1 | 3/2009 | Valaie |
| 2009/0105722 A1 | 4/2009 | Fulkerson |
| 2009/0105737 A1 | 4/2009 | Fulkerson |
| 2009/0131908 A1 | 5/2009 | McKay |
| 2009/0163846 A1 | 5/2009 | Aklog et al. |
| 2009/0177206 A1 | 7/2009 | Lozier et al. |
| 2009/0182336 A1 | 7/2009 | Brenzel et al. |
| 2009/0221967 A1 | 9/2009 | Thommen et al. |
| 2009/0270815 A1 | 10/2009 | Stamp et al. |
| 2009/0281610 A1 | 11/2009 | Parker |
| 2009/0292297 A1 | 11/2009 | Ferrere |
| 2009/0292307 A1 | 11/2009 | Razack |
| 2009/0299374 A1 | 12/2009 | Tilson et al. |
| 2009/0299393 A1 | 12/2009 | Martin |
| 2009/0306702 A1 | 12/2009 | Miloslavski |
| 2010/0004607 A1 | 1/2010 | Wilson et al. |
| 2010/0016957 A1 | 1/2010 | Jager et al. |
| 2010/0030186 A1 | 2/2010 | Stivland |
| 2010/0030256 A1 | 2/2010 | Dubrul et al. |
| 2010/0036312 A1 | 2/2010 | Krolik et al. |
| 2010/0087908 A1 | 4/2010 | Hilaire |
| 2010/0114017 A1 | 5/2010 | Lenker |
| 2010/0125326 A1 | 5/2010 | Kalstad |
| 2010/0125327 A1 | 5/2010 | Agnew |
| 2010/0137846 A1 | 6/2010 | Desai et al. |
| 2010/0191272 A1 | 7/2010 | Keating |
| 2010/0211094 A1 | 8/2010 | Sargent, Jr. |
| 2010/0249815 A1 | 9/2010 | Jantzen et al. |
| 2010/0268264 A1 | 10/2010 | Bonnett et al. |
| 2010/0268265 A1 | 10/2010 | Krolik et al. |
| 2010/0292726 A1 | 11/2010 | Olsen et al. |
| 2010/0305566 A1 | 12/2010 | Rosenblatt et al. |
| 2010/0305604 A1 | 12/2010 | Pah |
| 2010/0318178 A1 | 12/2010 | Rapaport et al. |
| 2010/0324649 A1 | 12/2010 | Mattsson |
| 2010/0331949 A1 | 12/2010 | Habib |
| 2011/0009875 A1 | 1/2011 | Grandfield et al. |
| 2011/0009940 A1 | 1/2011 | Grandfield et al. |
| 2011/0009942 A1 | 1/2011 | Gregorich |
| 2011/0022149 A1 | 1/2011 | Cox et al. |
| 2011/0054514 A1 | 3/2011 | Arcand |
| 2011/0054516 A1 | 3/2011 | Keegan |
| 2011/0060359 A1 | 3/2011 | Hannes |
| 2011/0071432 A1 | 3/2011 | Carrillo, Jr. et al. |
| 2011/0077620 A1 | 3/2011 | deBeer |
| 2011/0098683 A1 | 4/2011 | Wiita et al. |
| 2011/0054504 A1 | 5/2011 | Wolf et al. |
| 2011/0125181 A1* | 5/2011 | Brady ............ A61B 17/22031 606/200 |
| 2011/0130756 A1 | 6/2011 | Everson, Jr. et al. |
| 2011/0152920 A1 | 6/2011 | Eckhouse et al. |
| 2011/0160763 A1 | 6/2011 | Ferrera et al. |
| 2011/0166586 A1 | 7/2011 | Sepetka et al. |
| 2011/0196414 A1 | 8/2011 | Porter et al. |
| 2011/0202088 A1 | 8/2011 | Eckhouse et al. |
| 2011/0213290 A1 | 9/2011 | Chin et al. |
| 2011/0213297 A1 | 9/2011 | Aklog et al. |
| 2011/0213393 A1 | 9/2011 | Aklog et al. |
| 2011/0213403 A1 | 9/2011 | Aboytes |
| 2011/0218564 A1 | 9/2011 | Drasler et al. |
| 2011/0224707 A1 | 9/2011 | Miloslavski et al. |
| 2011/0264132 A1 | 10/2011 | Strauss et al. |
| 2011/0276120 A1 | 11/2011 | Gilson et al. |
| 2011/0288529 A1 | 11/2011 | Fulton |
| 2011/0319917 A1 | 12/2011 | Ferrera et al. |
| 2012/0041449 A1 | 2/2012 | Eckhouse et al. |
| 2012/0041474 A1 | 2/2012 | Eckhouse et al. |
| 2012/0059356 A1 | 3/2012 | diPama et al. |
| 2012/0089216 A1 | 4/2012 | Rapaport et al. |
| 2012/0101510 A1 | 4/2012 | Lenker et al. |
| 2012/0116351 A1 | 5/2012 | Chomas et al. |
| 2012/0116440 A1 | 5/2012 | Leynov et al. |
| 2012/0143237 A1 | 6/2012 | Cam et al. |
| 2012/0143239 A1 | 6/2012 | Aklog et al. |
| 2012/0150147 A1 | 6/2012 | Leynov et al. |
| 2012/0165858 A1 | 6/2012 | Eckhouse et al. |
| 2012/0165859 A1 | 6/2012 | Eckhouse et al. |
| 2012/0215250 A1 | 8/2012 | Grandfield et al. |
| 2012/0277788 A1 | 11/2012 | Cattaneo |
| 2012/0283768 A1 | 11/2012 | Cox et al. |
| 2012/0296362 A1 | 11/2012 | Cam et al. |
| 2012/0316600 A1 | 12/2012 | Ferrera et al. |
| 2013/0006284 A1 | 1/2013 | Aggerholm et al. |
| 2013/0025934 A1 | 1/2013 | Aimi et al. |
| 2013/0030461 A1 | 1/2013 | Marks et al. |
| 2013/0046330 A1 | 2/2013 | McIntosh et al. |
| 2013/0046333 A1 | 2/2013 | Jones et al. |
| 2013/0046334 A1 | 2/2013 | Jones et al. |
| 2013/0116774 A1 | 5/2013 | Strauss et al. |
| 2013/0131614 A1 | 5/2013 | Hassan et al. |
| 2013/0144326 A1 | 6/2013 | Brady et al. |
| 2013/0144328 A1 | 6/2013 | Weber et al. |
| 2013/0158592 A1 | 6/2013 | Porter |

(56) References Cited

U.S. PATENT DOCUMENTS

| | | |
|---|---|---|
| 2013/0184703 A1 | 7/2013 | Shireman et al. |
| 2013/0184739 A1 | 7/2013 | Brady et al. |
| 2013/0197567 A1 | 8/2013 | Brady et al. |
| 2013/0226146 A1 | 8/2013 | Tekulve |
| 2013/0268050 A1 | 10/2013 | Wilson et al. |
| 2013/0281788 A1 | 10/2013 | Garrison |
| 2013/0289697 A1 | 10/2013 | Baker et al. |
| 2013/0325055 A1 | 12/2013 | Eckhouse et al. |
| 2013/0325056 A1 | 12/2013 | Eckhouse et al. |
| 2013/0345739 A1* | 12/2013 | Brady ............ A61B 17/320725 606/200 |
| 2014/0012281 A1 | 1/2014 | Wang et al. |
| 2014/0046359 A1 | 2/2014 | Bowman et al. |
| 2014/0052097 A1 | 2/2014 | Petersen et al. |
| 2014/0081243 A1 | 3/2014 | Zhou et al. |
| 2014/0121672 A1 | 5/2014 | Folk |
| 2014/0128905 A1 | 5/2014 | Molaei |
| 2014/0135812 A1 | 5/2014 | Divino et al. |
| 2014/0180377 A1 | 6/2014 | Bose et al. |
| 2014/0188127 A1 | 7/2014 | Dubrul et al. |
| 2014/0194919 A1 | 7/2014 | Losardo et al. |
| 2014/0200607 A1 | 7/2014 | Sepetka et al. |
| 2014/0200608 A1 | 7/2014 | Brady et al. |
| 2014/0236220 A1 | 8/2014 | Inoue |
| 2014/0257018 A1 | 9/2014 | Farnan |
| 2014/0257362 A1 | 9/2014 | Eldenschink |
| 2014/0276840 A1 | 9/2014 | Richter et al. |
| 2014/0276922 A1 | 9/2014 | McLain et al. |
| 2014/0277003 A1 | 9/2014 | Hendrick |
| 2014/0277053 A1 | 9/2014 | Wang et al. |
| 2014/0277079 A1 | 9/2014 | Vale et al. |
| 2014/0309657 A1 | 10/2014 | Ben-Ami |
| 2014/0309673 A1 | 10/2014 | Dacuycuy et al. |
| 2014/0330302 A1 | 11/2014 | Tekulve et al. |
| 2014/0343585 A1 | 11/2014 | Ferrera et al. |
| 2014/0364896 A1 | 12/2014 | Consigny |
| 2014/0371769 A1 | 12/2014 | Vale et al. |
| 2014/0371777 A1 | 12/2014 | Rudakov et al. |
| 2014/0371779 A1 | 12/2014 | Vale et al. |
| 2014/0371780 A1 | 12/2014 | Vale et al. |
| 2014/0379023 A1 | 12/2014 | Brady et al. |
| 2015/0018859 A1 | 1/2015 | Quick et al. |
| 2015/0018860 A1 | 1/2015 | Quick et al. |
| 2015/0080937 A1 | 3/2015 | Davidson |
| 2015/0081003 A1 | 3/2015 | Wainwright et al. |
| 2015/0112376 A1 | 4/2015 | Molaei et al. |
| 2015/0133990 A1 | 5/2015 | Davidson |
| 2015/0142043 A1 | 5/2015 | Furey |
| 2015/0164523 A1 | 6/2015 | Brady et al. |
| 2015/0173782 A1 | 6/2015 | Garrison et al. |
| 2015/0173783 A1* | 6/2015 | Tah .................... A61B 17/221 606/127 |
| 2015/0238314 A1 | 8/2015 | Börtlein et al. |
| 2015/0250497 A1 | 9/2015 | Marks et al. |
| 2015/0257775 A1 | 9/2015 | Gilvarry et al. |
| 2015/0258270 A1 | 9/2015 | Kunis |
| 2015/0290437 A1 | 10/2015 | Rudakov et al. |
| 2015/0297252 A1 | 10/2015 | Miloslavski et al. |
| 2015/0306311 A1 | 10/2015 | Pinchuk et al. |
| 2015/0313617 A1 | 11/2015 | Grandfield et al. |
| 2015/0320431 A1 | 11/2015 | Ulm, III |
| 2015/0343178 A1 | 12/2015 | Fulton, III |
| 2015/0351770 A1 | 12/2015 | Fulton, III |
| 2015/0352325 A1 | 12/2015 | Quick |
| 2015/0359547 A1* | 12/2015 | Vale .................. A61M 25/0082 606/115 |
| 2015/0374391 A1 | 12/2015 | Quick et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022296 A1 | 1/2016 | Brady et al. |
| 2016/0066921 A1 | 3/2016 | Brady et al. |
| 2016/0074067 A1 | 3/2016 | Furnish et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0121080 A1 | 5/2016 | Cottone |
| 2016/0135829 A1 | 5/2016 | Holochwost et al. |
| 2016/0143653 A1 | 5/2016 | Vale et al. |
| 2016/0151079 A1 | 6/2016 | Aklog et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0228134 A1 | 8/2016 | Martin et al. |
| 2016/0256180 A1 | 9/2016 | Vale et al. |
| 2016/0262880 A1 | 9/2016 | Li et al. |
| 2016/0317168 A1 | 11/2016 | Brady et al. |
| 2016/0346002 A1 | 12/2016 | Avneri et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0065401 A1 | 3/2017 | Fearnot et al. |
| 2017/0071614 A1 | 3/2017 | Vale et al. |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086862 A1 | 3/2017 | Vale et al. |
| 2017/0086863 A1 | 3/2017 | Brady et al. |
| 2017/0086864 A1 | 3/2017 | Greenhalgh et al. |
| 2017/0086996 A1 | 3/2017 | Peterson et al. |
| 2017/0095138 A1 | 4/2017 | Nakade et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100142 A1 | 4/2017 | Look et al. |
| 2017/0100143 A1 | 4/2017 | Granfield |
| 2017/0100183 A1 | 4/2017 | Iaizzo et al. |
| 2017/0105743 A1 | 4/2017 | Vale et al. |
| 2017/0112515 A1 | 4/2017 | Brady et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172554 A1 | 6/2017 | Bortlein et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0238953 A1 | 8/2017 | Yang et al. |
| 2017/0239447 A1 | 8/2017 | Yang et al. |
| 2017/0252043 A1 | 9/2017 | Fuller et al. |
| 2017/0252064 A1 | 9/2017 | Staunton |
| 2017/0259042 A1* | 9/2017 | Nguyen ........... A61B 17/22032 |

(56) References Cited

U.S. PATENT DOCUMENTS

| | | |
|---|---|---|
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Sethna |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0008407 A1 | 1/2018 | Maimon et al. |
| 2018/0042623 A1 | 2/2018 | Batiste |
| 2018/0064526 A1 | 3/2018 | Walzman |
| 2018/0193050 A1* | 7/2018 | Hawkins ............... A61B 1/018 |
| 2018/0193591 A1 | 7/2018 | Jaroch et al. |
| 2018/0235644 A1 | 8/2018 | Jaffe et al. |
| 2018/0235743 A1 | 8/2018 | Farago et al. |
| 2018/0256177 A1 | 9/2018 | Cooper et al. |
| 2018/0303610 A1 | 10/2018 | Anderson |
| 2018/0368965 A1 | 12/2018 | Janardhan et al. |
| 2019/0021755 A1 | 1/2019 | Johnson et al. |
| 2019/0021759 A1 | 1/2019 | Krolik et al. |
| 2019/0029820 A1 | 1/2019 | Zhou et al. |
| 2019/0029825 A1 | 1/2019 | Fitterer et al. |
| 2019/0046219 A1 | 2/2019 | Marchand et al. |
| 2019/0192175 A1 | 6/2019 | Chida et al. |
| 2019/0209206 A1 | 7/2019 | Patel et al. |
| 2019/0216476 A1 | 7/2019 | Barry et al. |
| 2019/0239907 A1 | 8/2019 | Brady et al. |
| 2019/0247627 A1 | 8/2019 | Korkuch et al. |
| 2019/0255290 A1 | 8/2019 | Snyder et al. |
| 2019/0269491 A1 | 9/2019 | Jalgaonkar et al. |
| 2019/0274810 A1 | 9/2019 | Phouasalit et al. |
| 2019/0298396 A1* | 10/2019 | Gamba ............... A61B 17/221 |
| 2019/0365411 A1 | 12/2019 | Avneri et al. |
| 2019/0366049 A1 | 12/2019 | Hannon et al. |
| 2020/0009301 A1 | 1/2020 | Yee |
| 2020/0038628 A1 | 2/2020 | Chou et al. |
| 2020/0069912 A1 | 3/2020 | Tateshima |
| 2020/0155180 A1 | 5/2020 | Follmer |
| 2020/0008820 A1 | 6/2020 | Aboytes et al. |
| 2020/0205845 A1 | 7/2020 | Yang et al. |
| 2020/0214859 A1 | 7/2020 | Sherburne |
| 2020/0281611 A1 | 9/2020 | Kelly et al. |
| 2020/0281612 A1 | 9/2020 | Kelly et al. |
| 2020/0297972 A1 | 9/2020 | Yee et al. |
| 2020/0306501 A1 | 10/2020 | Yee et al. |
| 2020/0353208 A1* | 11/2020 | Merhi ............... A61M 25/0041 |
| 2020/0383698 A1 | 12/2020 | Miao et al. |
| 2021/0016213 A1 | 1/2021 | Takami et al. |
| 2021/0085935 A1 | 3/2021 | Fahey et al. |
| 2021/0128185 A1 | 5/2021 | Nguyen et al. |
| 2021/0153883 A1 | 5/2021 | Casey et al. |
| 2021/0153884 A1 | 5/2021 | Casey et al. |
| 2021/0154433 A1 | 5/2021 | Casey et al. |
| 2021/0162678 A1 | 6/2021 | Mori et al. |
| 2021/0219821 A1 | 7/2021 | Appling et al. |
| 2021/0307766 A1 | 10/2021 | Keating et al. |
| 2021/0393277 A1 | 12/2021 | Vale et al. |
| 2022/0117614 A1 | 4/2022 | Salmon et al. |
| 2022/0125450 A1 | 4/2022 | Sirhan et al. |
| 2022/0313426 A1 | 10/2022 | Gifford, III et al. |
| 2023/0054898 A1 | 3/2023 | Gurovich et al. |

FOREIGN PATENT DOCUMENTS

| | | |
|---|---|---|
| CN | 1972728 A | 5/2007 |
| CN | 103071195 A | 5/2013 |
| CN | 104507380 A | 4/2015 |
| CN | 104905873 A | 9/2015 |
| CN | 105007973 A | 10/2015 |
| CN | 105307582 A | 2/2016 |
| CN | 105726163 A | 7/2016 |
| CN | 106232059 A | 12/2016 |
| CN | 113040865 A | 6/2021 |
| DE | 202009001951 U1 | 4/2010 |
| DE | 102009056450 A1 | 6/2011 |
| DE | 102010010849 A1 | 9/2011 |
| DE | 102010014778 A1 | 10/2011 |
| DE | 102010024085 A1 | 12/2011 |
| DE | 102011014586 B3 | 9/2012 |
| DE | 20 2020 107013 U1 | 1/2021 |
| EP | 2301450 A1 | 3/2011 |
| EP | 2628455 A1 | 8/2013 |
| EP | 3302312 A1 | 4/2018 |
| EP | 3335647 A2 | 6/2018 |
| EP | 3 420 978 A1 | 1/2019 |
| EP | 4049704 A2 | 8/2022 |
| GB | 2498349 A | 7/2013 |
| JP | 9-19438 A | 1/1997 |
| JP | 2018501038 A | 1/2018 |
| WO | WO 93/04722 A2 | 3/1993 |
| WO | WO 94/24926 A1 | 11/1994 |
| WO | WO 97/27808 A1 | 8/1997 |
| WO | WO 97/38631 A1 | 10/1997 |
| WO | WO 99/20335 A1 | 4/1999 |
| WO | WO 99/56801 A2 | 11/1999 |
| WO | WO 99/60933 A1 | 12/1999 |
| WO | WO 01/21077 A1 | 3/2001 |
| WO | WO 02/02162 A2 | 1/2002 |
| WO | WO 02/11627 A2 | 2/2002 |
| WO | WO 02/43616 A2 | 6/2002 |
| WO | WO 02/070061 A1 | 9/2002 |
| WO | WO 02/094111 A2 | 11/2002 |
| WO | WO 03/002006 A1 | 1/2003 |
| WO | WO 03/018085 A2 | 3/2003 |
| WO | WO 03/030751 A1 | 4/2003 |
| WO | WO 03/051448 A2 | 6/2003 |
| WO | WO 2004/028571 A1 | 4/2004 |
| WO | WO 2004/056275 A1 | 7/2004 |
| WO | WO 2005/000130 A1 | 1/2005 |
| WO | WO 2005/027751 A1 | 3/2005 |
| WO | WO 2005/027779 A2 | 3/2005 |
| WO | WO 2006/021407 A2 | 3/2006 |
| WO | WO 2006/031410 A2 | 3/2006 |
| WO | WO 2006/107641 A2 | 10/2006 |
| WO | WO 2006/135823 A2 | 12/2006 |
| WO | WO 2007/054307 A2 | 5/2007 |
| WO | WO 2007/068424 A1 | 6/2007 |
| WO | WO 2008/034615 A2 | 3/2008 |
| WO | WO 2008/051431 A1 | 5/2008 |
| WO | WO 2008/131116 A1 | 10/2008 |
| WO | WO 2009/019664 A1 | 2/2009 |
| WO | WO 2009/031338 A1 | 3/2009 |
| WO | WO 2009/076482 A1 | 6/2009 |
| WO | WO 2009/086482 A2 | 7/2009 |
| WO | WO 2009/103125 A1 | 8/2009 |
| WO | WO 2009/105710 A1 | 8/2009 |
| WO | WO 2010/010545 A1 | 1/2010 |
| WO | WO 2010/046897 A1 | 4/2010 |
| WO | WO 2010/075565 A1 | 7/2010 |
| WO | WO 2010/102307 A1 | 9/2010 |
| WO | WO 2010/146581 A1 | 12/2010 |
| WO | WO 2011/013556 A1 | 2/2011 |
| WO | WO 2011/066961 A1 | 6/2011 |
| WO | WO 2011/082319 A1 | 7/2011 |
| WO | WO 2011/095352 A1 | 8/2011 |

(56) References Cited

FOREIGN PATENT DOCUMENTS

| | | |
|---|---|---|
| WO | WO 2011/106426 A1 | 9/2011 |
| WO | WO 2011/110316 A1 | 9/2011 |
| WO | WO 2012/052982 A1 | 4/2012 |
| WO | WO 2012/064726 A1 | 5/2012 |
| WO | WO 2012/081020 A1 | 6/2012 |
| WO | WO 2012/110619 A1 | 8/2012 |
| WO | WO 2012/120490 A2 | 9/2012 |
| WO | WO 2012/156924 A1 | 11/2012 |
| WO | WO 2013/016435 A1 | 1/2013 |
| WO | WO 2013/072777 A2 | 5/2013 |
| WO | WO 2013/105099 A2 | 7/2013 |
| WO | WO 2013/109756 A2 | 7/2013 |
| WO | WO 2014/081892 A1 | 5/2014 |
| WO | WO 2014/139845 A1 | 9/2014 |
| WO | WO 2014/169266 A1 | 10/2014 |
| WO | WO 2014/178198 A1 | 11/2014 |
| WO | WO 2014/188300 A1 | 11/2014 |
| WO | WO 2015/061365 A1 | 4/2015 |
| WO | WO 2015/134625 A1 | 9/2015 |
| WO | WO 2015/179324 A2 | 11/2015 |
| WO | WO 2015/179377 A1 | 11/2015 |
| WO | WO 2015/189354 A1 | 12/2015 |
| WO | WO 2016/010995 A1 | 1/2016 |
| WO | WO 2017/004234 A1 | 1/2017 |
| WO | WO 2017/097616 A1 | 6/2017 |
| WO | WO 2018/178979 A1 | 10/2018 |
| WO | WO 2018/193603 A1 | 10/2018 |
| WO | WO 2019/064306 A1 | 4/2019 |
| WO | WO 2019/079296 A1 | 4/2019 |
| WO | WO 2020/139979 A1 | 7/2020 |
| WO | WO 2021/016213 A1 | 1/2021 |
| WO | WO 2021/162678 A1 | 8/2021 |
| WO | WO 2021/167653 A1 | 8/2021 |
| WO | WO 2022/020366 A2 | 1/2022 |

OTHER PUBLICATIONS

Vargas, J., et al. "Efficacy of beveled tip aspiration catheter in mechaincal thrombectomy for actue ischemic stroke" J NeuroIntervent Surg 0:1-5 (2020).

Struffert, T., et al. "Intravenous flat detector CT angiography for non-invasive visualisation of intracranial flow diverter: technical feasibility" Eur Radiol 21:1797-1801 (2011).

\* cited by examiner

BEVEL TIP EXPANDABLE MOUTH CATHETER WITH REINFORCING RING

FIELD OF INVENTION

The present invention generally relates devices and methods for removing acute blockages from blood vessels during intravascular medical treatments. More specifically, the present invention relates to retrieval catheters with expandable tips into which an object or objects can be retrieved.

BACKGROUND

Clot retrieval aspiration catheters and devices are used in mechanical thrombectomy for endovascular intervention, often in cases where patients are suffering from conditions such as acute ischemic stroke (AIS), myocardial infarction (MI), and pulmonary embolism (PE). Accessing the neurovascular bed in particular is challenging with conventional technology, as the target vessels are small in diameter, remote relative to the site of insertion, and highly tortuous. These catheters are frequently of great length and must follow the configuration of the blood vessels in respect of all branching and windings. Traditional devices are often either too large in profile, lack the deliverability and flexibility needed to navigate particularly tortuous vessels, or are not effective at removing a clot when delivered to the target site.

Many existing designs for aspiration retrieval catheters are often restricted to, for example, inner diameters of 6 Fr or between approximately 0.068-0.074 inches. Larger sizes require a larger guide or sheath to be used, which then necessitates a larger femoral access hole to close. Most physicians would prefer to use an 8 Fr guide/6 Fr sheath combination, and few would be comfortable going beyond a 9 Fr guide/7 Fr sheath combination. This means that once at the target site, a clot can often be larger in size than the inner diameter of the aspiration catheter and must otherwise be immediately compressed to enter the catheter mouth. This compression can lead to bunching up and subsequent shearing of the clot during retrieval. Firm, fibrin-rich clots can also become lodged in the fixed-mouth tip of these catheters making them more difficult to extract. This lodging can also result in shearing where softer portions breaking away from firmer regions of the clot.

Small diameters and fixed tip sizes are also less efficient at directing the aspiration necessary to remove blood and thrombus material during the procedure. The suction must be strong enough such that any fragmentation that may occur as a result of aspiration or the use of a mechanical thrombectomy device cannot migrate and occlude distal vessels. When aspirating with a fixed-mouth catheter, a significant portion of the aspiration flow ends up coming from vessel fluid proximal to the tip of the catheter, where there is no clot. This significantly reduces aspiration efficiency, lowering the success rate of clot removal.

Large bore intermediate and aspiration catheters and/or those with expandable tips are therefore desirable because they provide a large lumen and distal mouth to accept a clot with minimal resistance. The bore lumen of these catheters can be nearly as large as the guide and/or sheath through which they are delivered, and the expandable tip can expand to be a larger diameter still. When a clot is captured and drawn proximally into a tip with a funnel shape, the clot can be progressively compressed during retrieval so that it can be aspirated fully through the catheter and into a syringe or canister.

In many examples, the fixed-mouth catheters and those with expandable tips can have an underlying braid as the primary supporting backbone. The use of braids in catheter support is not a novel concept, and typical examples can be readily found in the art. The braid can often be as simple as bands wrapped spirally in one direction for the length of the catheter which cross over and under bands spiraled in the opposite direction. The bands can be metallic, fiberglass, or other material providing effective hoop strength to reinforce the softer outer materials of the body. However, supporting braids can also have a very high sectional stiffness the point where they do not meet the flexibility criteria for many procedures or cannot be made soft enough for use in fragile vessels without causing substantial trauma. Conversely, the low section stiffness and hoop strength of many braids means that, during an aspiration procedure, the applied suction can collapse the tip before a clot is engaged.

Further catheter advances have shown evidence that a larger aspiration catheter tip surface area can lead to increased aspiration efficiency and an enhanced interface with a clot. Designs with angled bevel tips have been shown to improve interaction with a lodged clot, as a beveled tip offers a larger mouth area for aspiration and ingestion than a flat tip. An in vitro study by Vargas et al. demonstrated an improvement of nearly 70% in the incidence of complete ingestion of a clot when using a bevel tip catheter compared to a flat tip control device (Vargas et al., Journal of Neuro-Interventional Surgery 2021; 13:823-826). As such, there is potential that a beveled tip can reduce the total number of aspiration attempts for a successful procedure, reduce the added complication associated with stentriever usage, and/or lead to more frequent TICI 2C revascularization grades with lower mRS scores. Despite this, greater support can be required to prevent tip collapse due to the reduced hoop stiffness resulting from an annular beveled shape as compared to a right cylinder.

As a result, the tip must be compliant enough to be advanced easily through a guide or sheath in a collapsed state, while being strong enough to withstand aspiration forces without collapsing. Combining these needs without significant tradeoffs can be tricky. There remains a need for improved catheter designs attempting to overcome these design challenges. The presently disclosed designs provide devices and methods capable of addressing the above-stated deficiencies.

SUMMARY

It is an object of the present designs to provide devices and methods to meet the above-stated needs. The designs can be for a clot retrieval catheter capable of remove a clot from cerebral arteries in patients suffering AIS, from coronary native or graft vessels in patients suffering from MI, and from pulmonary arteries in patients suffering from PE, or from other peripheral arterial and venous vessels in which a clot is causing an occlusion. The designs can also resolve the challenges of aspirating clot material utilizing an expandable tip capable of the suction energy/work required to deform these clots while having the structure to resist collapse during the procedure.

In some examples, a catheter can have a proximal elongate shaft with a proximal end, a distal end, a large internal bore, and a longitudinal axis extending therethrough. The elongate shaft can have a shaft braid configured around a low friction inner liner. The braids can serve as the backbone and support for the catheter shaft. The interlacing weave of the braid can be any number of materials or patterns known in the art and can have a varied density and composition along the length of the shaft.

In many examples, the catheter can have an expandable distal tip section extending from the distal end of the elongate shaft. The tip section can have a collapsed delivery configuration and an expanded deployed configuration. The tip can be radially collapsed for delivery through an outer guide sheath and can assume a funnel shape profile in the expanded configuration. The tip can have an outer polymeric membrane or jacket supported by an underlying braid. The distal end of the tip section can have a reinforcing ring on the braid and define a mouth that has a beveled profile forming an angle not perpendicular to the longitudinal axis of the catheter. The ends of the braid can be cut, or the wires can follow one spiral direction distally and then invert proximally back on themselves at the distal end to form the other spiral direction. The braid of the expandable distal tip section can accommodate radial expansion, and therefore can have variable PPI and cell angles to balance allowable expansion of the funnel tip with radial force capabilities.

The tip and shaft braids and can be monolithically formed or joined separately. In some examples, the tip and shaft braids can be made from the same material, or they can be different materials. In one example, the distal wires of the tip braid can be of Nitinol or another shape memory superelastic alloy composition allowing them to be heat set to the desired expanded diameter of the tip during manufacturing.

In other examples, the tip and shaft braids can have wires of differing thickness so that there is a hinging effect between the distal tip and the shaft while navigating the catheter through bends in the anatomy. A hinge can allow the distal tip section to be kept relatively short to reduce the tendency to elongate or shorten under tensile or compressive loading.

Longitudinally, the elastically expanded shape of the tip can be a substantially funnel shape flared radially from the shaft, so that in the transverse plane the tip section has a circular cross section in both the collapsed delivery configuration and the expanded deployed configuration. In one case, the circular profile of the tip section in the collapsed delivery configuration can define a center which is coincident with the longitudinal axis of the elongate body. Alternately, the circular profile of the tip section in the expanded deployed configuration can result in a center that is radially offset from the longitudinal axis.

The reinforcing ring can be disposed around the perimeter of the distal mouth of the expandable distal tip section. At least a portion of the ring can define a mouth plane forming an acute angle with respect to the longitudinal axis of the catheter when the distal tip section is in the collapsed delivery configuration. This angle can be similar or different when the tip section is deployed to the expanded configuration. In one example, the angle can be in a range between approximately 30 degrees and approximately 60 degrees. In another more specific instance, the angle can be approximately 45 degrees, The reinforcing ring can be polymeric, metallic, or other suitable materials capable of adding stiffness and shape to the distal end of the tip section. In a preferred example, the reinforcing ring can be a shape memory alloy such as Nitinol which can be heat set to a desired expanded inner diameter larger than a collapsed inner diameter when the distal tip section is in the expanded deployed configuration. In another example, the reinforcing ring can overmolded to the braid. In a further alternative, the ring can be PVC or other appropriate density polymer.

During manufacturing, the reinforcing ring can be welded to the distal braid of the tip section. In other examples, brazing, friction welding, adhesives, or other means can be used to attach the reinforcing ring.

To facilitate consistent expansion and folding of the expandable tip section, the reinforcing ring can have a plurality of relief features in the circumferential profile. In some designs, the relief features can be machined into the ring, or the ring can be formed in a mold to have the features. The braid wires of the tip braid can be cut to follow the contours of the relief features at the distal end of the tip section. In another case, the braid wires can be wound around the perimeter and relief features of the reinforcing ring.

The features can be, for example, keyhole shapes having a parallel section and a rounded section extending proximally from the distal edge of the perimeter of the reinforcing ring. In another case, the relief features can be axial slots or other geometry extending proximally from the distal perimeter of the mouth formed by the reinforcing ring. The features can have portions which are parallel to the longitudinal axis or form an angle with respect to the axis.

The features can reduce the cross section profile of at least a portion of the tip section. The features can also be axially or longitudinally offset from the oblique mouth plane. This effective reduction in material due to the relief features encourages folding along specific planes around the circumference of the tip. The features can be spaced equally around the ring circumference such that the folding during collapse into an outer sheath is symmetric about the longitudinal axis. Alternatively, the features can be intermittently spaced so that folding is encouraged along certain planes advantageously. In addition, the relief features can form an angle with the axis in order to bias the collapse of the tip section in certain directions.

Other catheter designs of the present disclosure can have a proximal elongate shaft having proximal end, a distal end, and a tubular shaft braid defining a lumen and a longitudinal axis extending therethrough. The shaft can terminate distally at a radiopaque marker band. An expanding distal tip section can be disposed at the distal end of the elongate shaft and have a supporting tip braid and a reinforcing ring attached to the distal end of the tip braid.

The marker band can be a radiopaque material or can include a radiopaque coating or filler material. The material can be compatible with the materials of the shaft braid and tip braid so that the braid ends can be welded or otherwise attached to the marker band and the band serves as a joint between sections. In some examples, the proximal end of the supporting tip braid can be welded to the marker band. In another example, the distal end of the shaft braid can be welded to the marker band. In further examples, welding or adhesives are used to connect the shaft braid to the tip braid and the combined structure can be attached to the band.

The distal tip section can have a collapsed delivery configuration and an expanded deployed configuration. The reinforcing ring at the distal end of the tip section can have a plurality of relief features or cutouts spaced equally around the longitudinal axis. The cutouts can reduce the cross sectional profile around the perimeter of the reinforcing ring. At least a portion of the reinforcing ring can be planar to define a mouth plane which forms an acute angle with the axis when the tip section is in the collapsed delivery configuration, the expanded deployed configuration, or both. At least a portion of each of the relief features can be offset from the mouth plane so as to extend proximally from the mouth plane.

The profile of the distal tip section can be substantially symmetric with respect to the longitudinal axis when in the collapsed delivery configuration, but asymmetric or offset when in the expanded deployed configuration. A center of the expanded tip can be radially offset from a center of the catheter shaft.

Polymer membranes or jackets can be wrapped around the shaft braid and the tip braid. The jackets can be placed in an axial series and be selected from materials that are melt-miscible with each other so that adjacent layers help to hold together the underlying braid between them. Materials can also be chosen so that the stiffness of different sections of the catheter can be varied in a stepwise or continuous fashion. The cooperation between the braids and the polymer jackets can yield a catheter which has both a thin wall but is also highly kink resistant.

Some or all of the distal tip section can be covered or encapsulated within a distalmost tip jacket. The tip jacket can be of a very soft material so as to have the most atraumatic vessel crossing profile. For example, a low durometer Pebax can be used having a hardness is the range of approximately 42 Shore A to approximately 72 Shore A. Alternatively, a Neusoft layer can be reflowed to encapsulate the tip of 62 Shore A or even 42 Shore A.

The distalmost polymer tip jacket can be trimmed to follow the contours of the reinforcing rings around the mouth of the tip section of the catheter. The distal edge of the tip jacket can mirror that of the reinforcing ring including circumferential gaps to follow the outline of the relief features of the ring. In an alternate example, the tip jacket can be trimmed to a circular or ovular end of the beveled tip but be webbed over the cutouts of the relief features. A further design can have the tip jacket extending distally beyond the distal edge contours of the reinforcing ring as a soft lip overhanging the ring.

Other aspects of the present disclosure will become apparent upon reviewing the following detailed description in conjunction with the accompanying figures. Additional features or manufacturing and use steps can be included as would be appreciated and understood by a person of ordinary skill in the art.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation. It is expected that those of skill in the art can conceive of and combine elements from multiple figures to better suit the needs of the user.

DETAILED DESCRIPTION

Specific examples of the present invention are now described in detail with reference to the Figures. The designs herein can be for a clot retrieval catheter with a large internal bore and a distal tip section that can self-expand to a substantially funnel shape with a diameter larger than that of the guide or sheath through which it is coaxially delivered. The designs can have a proximal elongate body for the shaft of the catheter, and a distal tip with an expanding braided support structure and outer polymeric jacket to give the tip atraumatic properties. The tip section can have a reinforcing ring at the distal end which serves to add hoop strength and prevent the braid and jacket from collapsing under the suction of aspiration. The catheter's tip designs can also be sufficiently flexible to navigate highly tortuous areas of the anatomy while being able to recover its shape and maintain the inner diameter of the lumen when collapsed into a delivery configuration or displaced in a vessel.

Accessing the various vessels within the vascular, whether they are coronary, pulmonary, or cerebral, involves well-known procedural steps and the use of a number of conventional, commercially-available accessory products. These products, such as angiographic materials, mechanical thrombectomy devices and stentrievers, microcatheters, and guidewires are widely used in laboratory and medical procedures. When these products are employed in conjunction with the devices and methods of this invention in the description below, their function and exact constitution are not described in detail. Additionally, while the description is sometimes in the context of thrombectomy treatments in intercranial arteries, the disclosure may be adapted for other procedures and in other body passageways as well.

Figure 1:
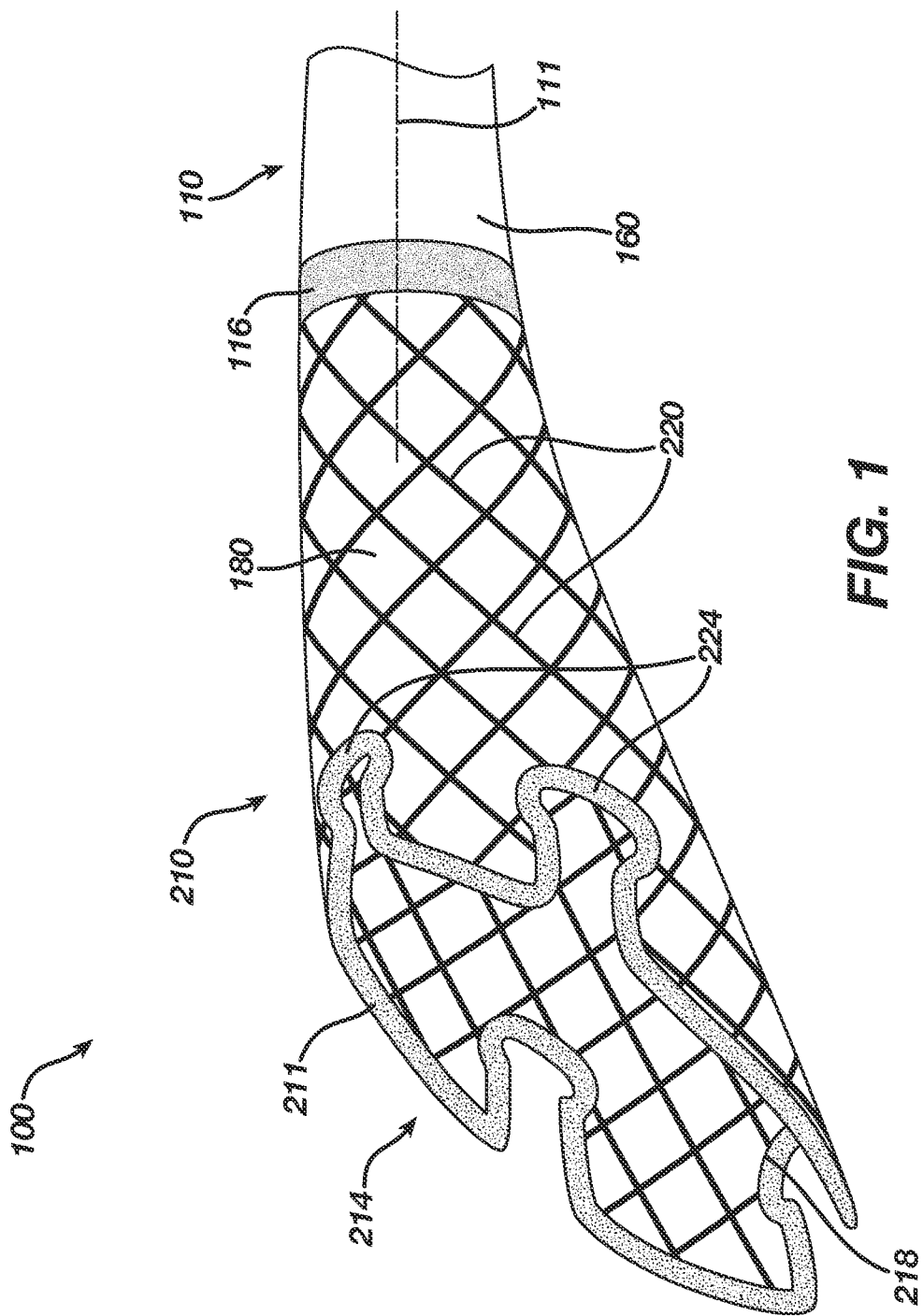
FIG. 1 is a view of a distal portion of a clot retrieval catheter with an expandable tip according to aspects of the present invention.

Turning to the figures, FIG. 1 illustrates a clot retrieval catheter 100 of the designs disclosed herein. The catheter can have an elongate shaft 110 and a tip section 210 attached distally thereto. The tip section 210 can radially expand to provide better aspiration efficiency and a larger distal mouth 218 for ingesting an occlusive clot. The mouth 218 of the tip section can be provided with a slanted or beveled distal surface at an angle with the longitudinal axis 111, which presents an oblique mouth with an even greater area for aspiration and clot ingestion. A reinforcing ring 211 can be incorporated at the distal end 214 of the tip section 210 to retain the braid 220 structure of the tip in an expanded funnel shape during aspiration and facilitate wrap down when withdrawn into an outer sheath. The catheter can have one or more radiopaque marker bands 116 to identify various transition points and terminal ends of the device during a procedure.

The braided sections of the shaft and the tip can be formed monolithically or in discrete sections. In many cases, four or more discrete braided sections of differing flexibility can be used. It can be appreciated that the different braided sections of the tip and shaft braids can have different geometries and weave patterns to achieve desired properties for that portion of catheter. Through choice of physical parameters and materials, different flexibility and stiffness characteristics can thus be given to different sections of the catheter 100 to meet clinical requirements.

The elongate shaft can have a backbone consisting of shaft braid sections and enclosed by an axial series of outer body jackets 160. Similarly, the tip section 210 can have tip braid 220 surrounded by one or more polymeric tip jackets 180. The jackets can be made of various medical grade polymers known in the art, such as PTFE, polyether block amide (Pebax®), or Nylon.

The braid 220 in the distal tip section 210 can have nitinol wires formed into the expanded free shape of the funnel profile when expanded. Nitinol braid wires like those of the tip braid can be used for the proximal braid 120 of the shaft 110 as well, but less expensive stainless steel wires can also be substituted to perform in these regions for stiffness and with less cost.

As used herein, "braided sections", "braids", and similar terms are used collectively to describe the support structure for the catheter shaft and tip. This type of catheter construction is commonly known in the art. The terms can refer to segments within a single monolithic braid that have different physical properties (PIC count, braid angle, etc.) and/or configurations and does not necessarily mean two distinct structures bonded together. Alternately, the terms can refer to a collective of distinct sections which are knitted together.

The marker band 116 can be positioned at or on the distal end of the shaft 110 and the proximal end of the tip section 210. The marker band can be platinum, gold, and/or another metallic collar, or alternatively can be coated with a compound giving substantial radiopacity. The band can be kept relatively short in length, for example between 0.3-1.0 mm, in order to minimize the impact on shaft flexibility. The band 116 can be crimped in place on a mandrel and later adhered to the ends of braided sections. In some examples, the band 116 can also function as a joint between the braids of the tip section 210 and the shaft 110, allowing for the braided sections of each to be quickly manufactured separately to any of a number of desired lengths and joined together at the band. If the catheter length is the typical 1350 mm of many designs, the tip section 210 can be approximately 100 mm in length, leaving a 1250 mm shaft 110 terminating at a proximal luer. The use of specific metallics such as platinum (which can be welded to both stainless steel and Nitinol) for the sleeve of the marker band 116 can replace the use of adhesives or other means and create a more robust joint.

The lumen of the catheter shaft can be sized so the catheter 100 is compatible with commonly-sized and readily available guide sheaths. A low friction inner liner can be disposed beneath the braid 120, facilitating use of the lumen for the delivery of auxiliary devices, contrast injection, and direct distal aspiration to a clot face. Preferred liner materials can be fluoropolymers such as polytetrafluoroethylene (PTFE or TFE), ethylene-chlorofluoroethylene (ECTFE), fluorinated ethylene propylene (FEP), polyvinyl fluoride (PVF), or similar materials. Depending on the material chosen, the liner can also be stretched to alter the directionality of the liner material (e.g., if the liner material has fibers, an imposed stretch can change a nominally isotropic sleeve into a more anisotropic, longitudinally-oriented composition) to reduce the wall thickness as required.

The body jackets 160 and tip jackets 180 can be butted together to form a continuous and smooth outer surface for the catheter shaft. The polymeric jackets can be reflowed or laminated in place along the length of the elongate shaft 110 and tip section 210. The applied heat can allow the outer polymer to fill the interstitial sites between the braids. This flow can also help to fix the jackets axially so they cannot slide distally.

These outer jackets can have varying durometer hardness to create, in conjunction with the braided structures, a proximal portion of the catheter with more column stiffness (by durometer hardness, flexure modulus, etc.) and transition into a distal portion with more lateral flexibility. In some examples, the body jackets can have a hardness in the range between approximately 25 to approximately 72 Shore D. The tip jacket 180 or jackets can have a distalmost jacket with the least stiffness for the most atraumatic vessel crossing profile.

Figure 2:
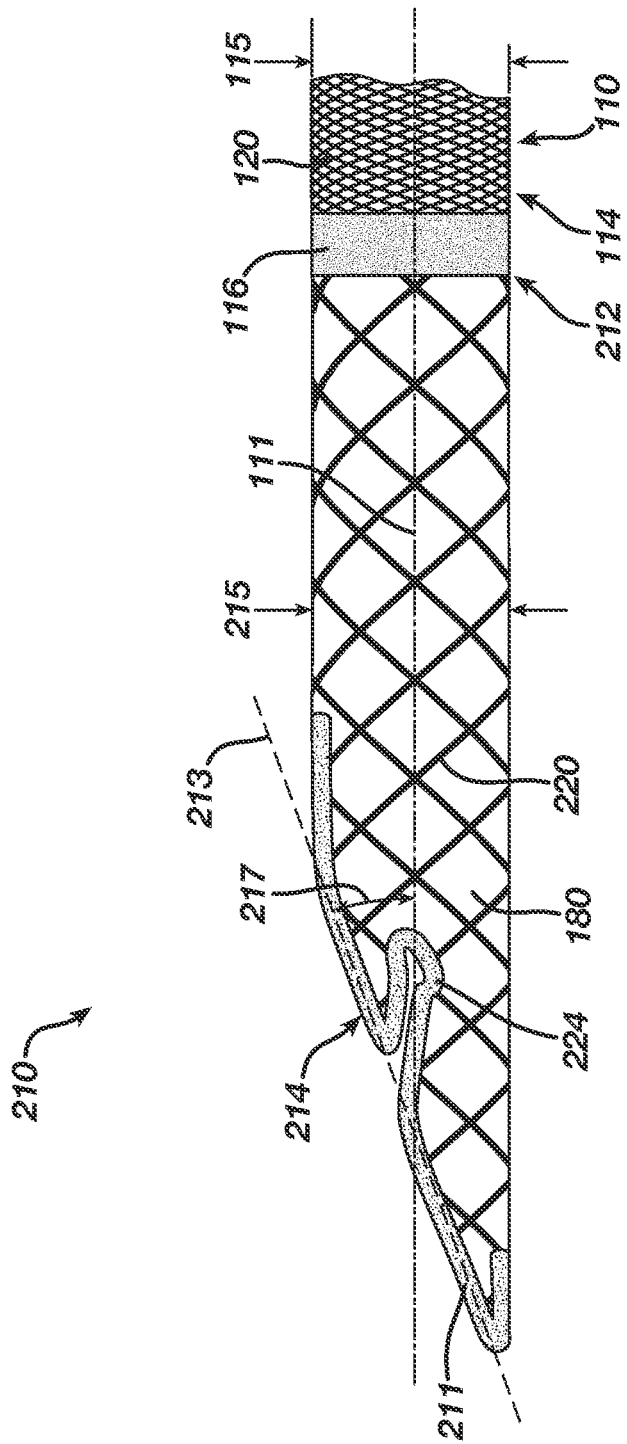
FIG. 2 illustrates a side view of the catheter of FIG. 1 according to aspects of the present invention.

FIG. 2 shows a profile view of the distal portion of the catheter 100 of FIG. 1. As disclosed, a distal marker band 116 approximately 0.8 mm in length can be included just proximal of the polymeric tip jacket 180 to give radiopacity near the distal end 214 of the tip section 210. The marker band 116 can be platinum or another suitable noble metal and can be crimped over, under, or between the assembly of the braids 120, 220 of the shaft 110 and tip section 210. The band 116 can also be situated at or near the distal end 114 of the shaft and at least 5 mm and up to 10 mm or more from the distal end 214 of the tip section 210. Alternatively, or in addition, the reinforcing ring 211 of the distal tip section 210 can also be constructed of radiopaque material or be coated or embedded with such material to illuminate the final distal terminus of the device when interacting with a clot.

The catheter shaft 110 can have one or more axial spines (not shown) extending with the shaft braid 120 along the longitudinal axis 111. The spine or spines 117 can counteract tensile elongation and contribute to the push characteristics of the shaft. This can be especially beneficial for when a large stiff clot becomes lodged at the distal end of the catheter and subjects the spine 110 to large tensile forces as the catheter is retracted into a larger outer sheath for removal from the vessel. The spine can be positioned beneath the braid, threaded between weaves of the braid, located on the outer diameter of the braid, or some combination of these. The spine can be composed of metallics, a polymeric, or composite strands such as Kevlar. In other examples, the spine can be a thread or other structure capable of supporting tensile loads but not compressive loads. In some preferred examples a liquid crystal polymer (LCP), such as Technora, can be utilized which is easy to process and offers high tensile strength without sacrificing any lateral flexibility.

When the catheter 100 is transiting to the target site or being retracted back into an access catheter/outer sheath in the collapsed delivery configuration shown, the tip section 210 can be wrapped radially down to compress the braid 220 and fold at the location of the relief features 224 around the circumference of the reinforcing ring 211. In the access catheter, the tip section 210 can have a collapsed inner diameter 215 that is the same or nearly the same as the inner diameter 115 of the elongate shaft 110.

As shown in FIG. 1 and FIG. 2, the distal end 214 of the tip section 210 can have a beveled surface inclined at an angle 217 with respect to the longitudinal axis 111. A beveled surface can increase aspiration efficiency and present a larger mouth area for improved clot ingestion, which can result in improved reperfusion and recanalization outcomes when compared to catheters with non-beveled tips. As such, a beveled tip can potentially reduce the number of passes required for a successful procedure or reduce the added complication involved with the introduction of mechanical clot retrieval devices.

When the tip section 210 is in the collapsed state, the beveled distal surface of the annular mouth 218 of the tip section 210 can reside on an inclined plane 213 at an acute angle 217 with the longitudinal axis 111. The plane 213 can reside at an angle of at least approximately 10 degrees up to at least 60 degrees with respect to the axis. For a more atraumatic profile during navigation, a preferable angle 217 can be in a range from approximately 30 degrees to 60 degrees, or, more specifically, can be approximately 45 degrees.

To be compatible with whichever widely adopted outer guide and/or sheath is chosen, the inner diameter 115 of the catheter shaft 110 and the collapsed inner diameter 215 of the expandable tip section 210 can be sized and scaled appropriately. The cross sections of the tip section and shaft can be largely symmetric when collapsed, so that for example a 5 Fr catheter targeting vessels approximately 2.0 mm in diameter can have shaft/tip inner diameters 115, 215 of approximately 0.054 inches. Similarly, a 6 Fr catheter targeting vessels approximately 2.3-3.4 mm in diameter can have shaft/tip inner diameters 115, 215 of approximately 0.068-0.074 inches. A larger nominally 8 Fr catheter for less remote clots can have shaft/tip inner diameters 115, 215 of approximately 0.082-0.095 inches. In most situations, the actual design upper bounds of the tip diameter 215 when collapsed is limited by friction and other delivery forces when traversing within an outer guide or sheath.

Figure 3:
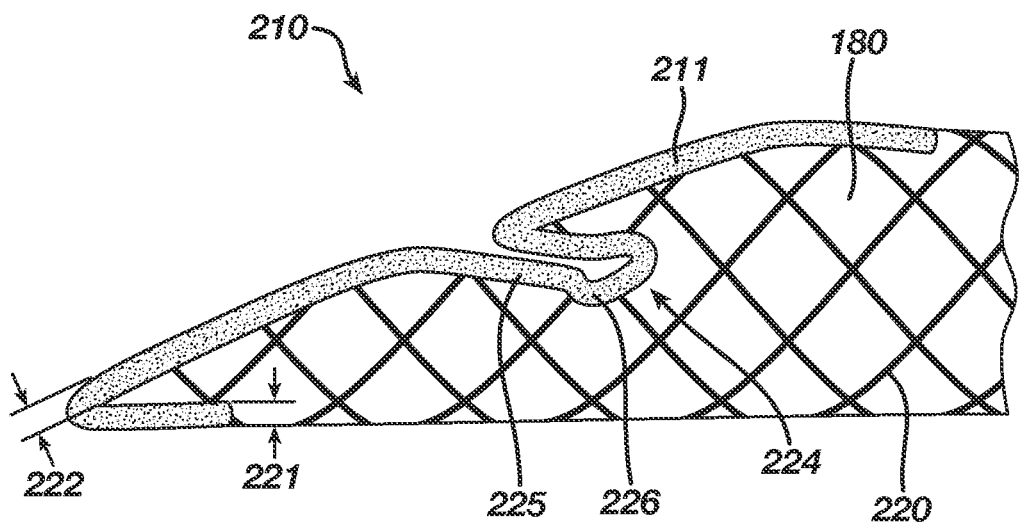
FIG. 3 shows a close in view of the catheter tip section of FIG. 2 in the collapsed delivery configuration according to aspects of the present invention.

The reinforcing ring can have a variety of shapes determining the profile of the distal end 214 of the tip section 210, as seen in a closer view of the collapsed tip illustrated in FIG. 3. The ring 211 can be affixed around the distal edge of the tip braids 220 through welding or brazing. In one example, the reinforcing ring 211 can be a nitinol member which tightly grips the underlying braid and is set to a free shape which elastically stretches the distal portion of the tip section radially when sprung to a larger diameter in the deployed condition outside of a guide or sheath. Alternately, the ring 211 can be polymeric and overmolded, injection molded, or spray or dip coated onto the braided layer using masking.

The length and contour of the tip section 210 as tapered in a substantially funnel shape from the distal end 214 when expanded can be tailored through the design of the pattern of the tip braid 220 and reinforcing ring 211. As mentioned, the wires of the braid 220, in addition to or instead of the ring element, can have shape memory characteristics and heat set to the designed elastic free shape desired. For example, a shorter funnel section can offer the benefits of good hoop stiffness and flexibility through having a shorter lever distance to hinge off the elongate shaft 110. Additionally, a shorter funnel can also be tailored to minimize stretch and deformation in the more distal of the outer polymer tip jackets 180. Alternatively, a longer funnel with a shallower taper can better interact with and more gradually compress a clot over the length of the tip to reduce the risk of lodging.

The reinforcing ring 211 can be formed as a single piece of uniform thickness or can be varied in thickness at particular sections. In FIG. 3, the ring 211 can have a slightly greater thickness 221 to stiffen the web or ligaments between the relief features 224, as these sections make up the majority of the mouth perimeter and can provide the greatest radial force to resist aspiration forces. The ring 211 can transition to a lesser thickness 222 in the region of the relief features 224 to further bias folding and collapse of the tip along these planes. The tip jacket 180 can also be trimmed to follow the contours of the reinforcing ring 211 (including trimmed proximally around the relief features 224) so as not to add further stiffness in these regions while maintaining symmetry in folding.

The relief features 224 can be a keyhole-shaped protrusions extending proximally from the distal perimeter of the reinforcing ring 211 at the catheter mouth 218. A keyhole shape can have two parallel sections 225 running from the beveled annular portion of the ring 211 and terminating in a rounded section 226 acting as a stress reducer and articulating enabler for the ring structure. The keyhole relief features 224 allow the ring "open" and "close" by hinging about the rounded section 226, enabling the distal tip 210 expand and collapse repeatedly without failure. The interrupting nature of the relief features 224 around the mouth 218 means they also function as flanges or keys during and post-manufacturing to aid in locating and securing the reinforcing ring 211 to the underlying braid 220.

Figure 4:
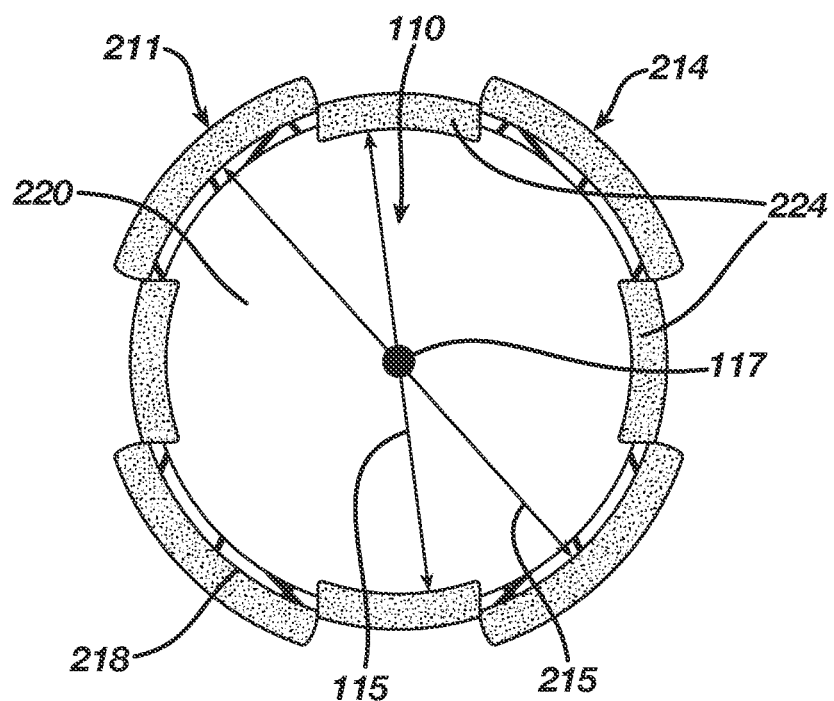
FIG. 4 depicts an end on view of the catheter tip section of FIG. 3 according to aspects of the present invention.

FIG. 4 depicts an end on view of the distal tip section 210 in the collapsed delivery configuration. When constrained within an outer sheath, the collapsed inner diameter 215 of the tip section can be approximately equal to the inner diameter 115 of the shaft 110. Depending on the final design profile of the reinforcing ring 211, the tip section and shaft can be concentric about a common center 117 when the tip is collapsed, or they can be offset. The annular mouth 218 can be an ellipse residing on the beveled plane inclined from the longitudinal axis 111.

Figure 5:
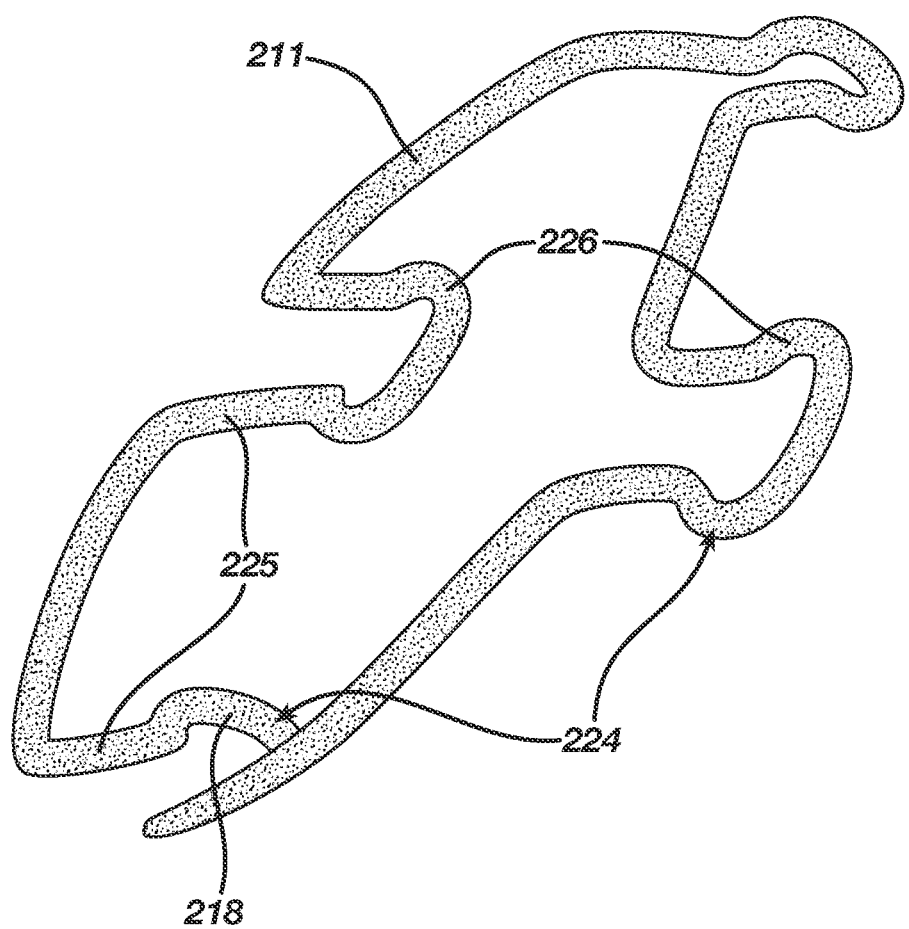
FIG. 5 shows a reinforcing ring of the catheter tip section according to aspects of the present invention.

Four relief features 224 spaced 90 degrees apart, as seen in the perspective view of the reinforcing ring 211 in FIG. 5, help the tip section 210 to wrap down evenly and symmetrically while maintaining the inner diameter of the mouth 218 for use with ancillary devices. It should be noted that a larger or smaller number of relief features can be anticipated. The features can be spaced evenly around the longitudinal axis to promote symmetric folding of the tip section. For example, six relief features can be employed spaced 30 degrees apart. Alternatively, in some other examples, the reinforcing ring 211 can incorporate an odd number or relief features, or the features can be spaced in a non-symmetric fashion around the mouth so as to bias folding in certain directions of planes.

Figure 6:
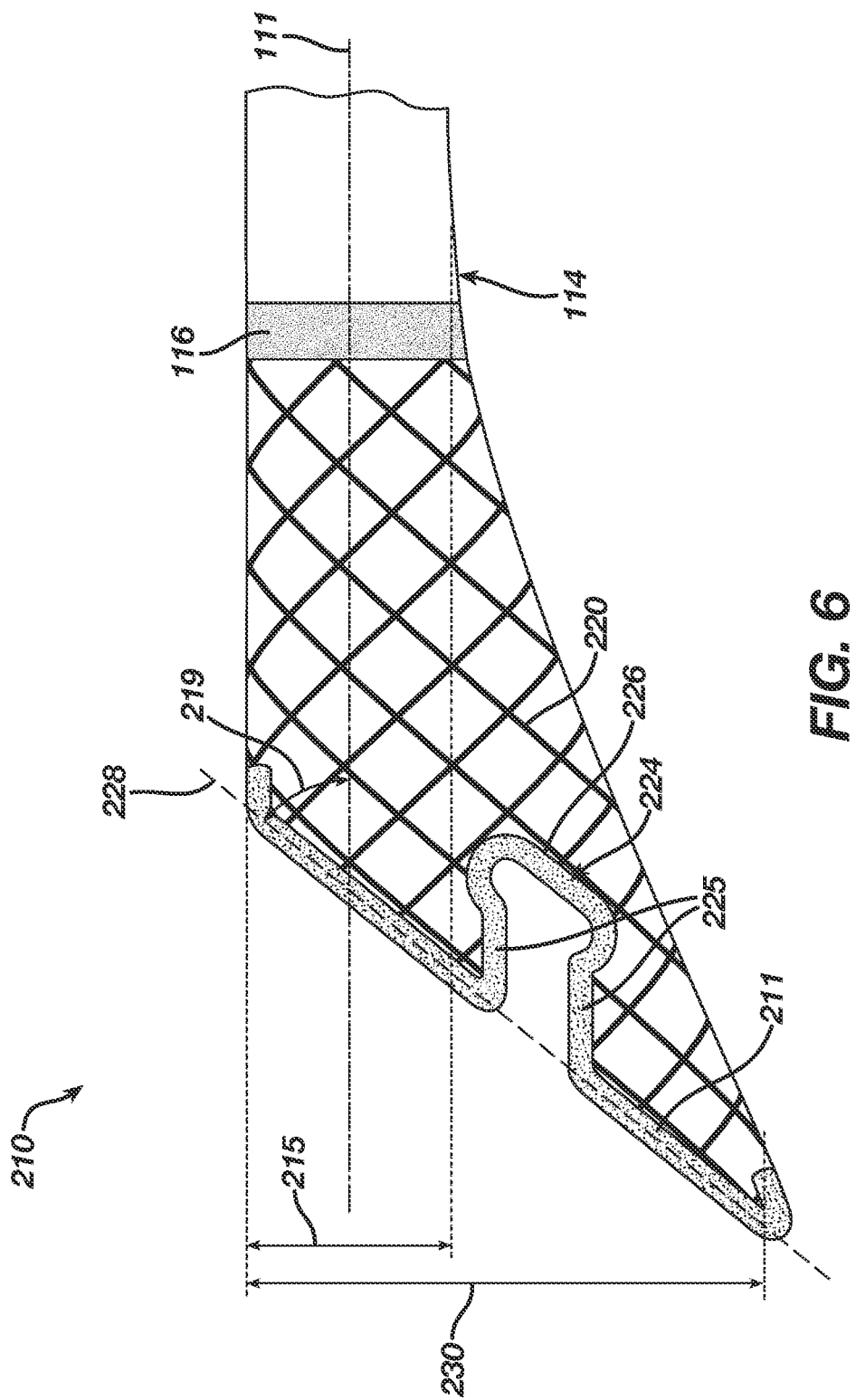
FIG. 6 illustrates the catheter tip section of FIG. 2 in the expanded deployed configuration according to aspects of the present invention.

The keyhole shaped relief features 224 of this example of the reinforcing ring 211 can each have two parallel sections 225 joined proximally by a rounded section 226. Each relief feature can thus serve as an aperture allowing radial expansion of the tip section. As illustrated in FIG. 6, the mouth 218 of the tip section 210 can expand from a collapsed diameter 215 to a larger inner diameter 230 in the expanded deployed configuration. The beveled distal end can define an expanded mouth plane 228 inclined at an acute angle 219 with respect to the longitudinal axis 111. The beveled profile allows for a larger inlet area for ease of ingesting firm clots and allows the clot to be compressed more gradually over a greater length of the tip, improving the chances of the clot can be completely ingested and aspirated through the shaft of the catheter.

One or both of the reinforcing ring 211 and the wires of the tip braid 220 can be Nitinol or another shape memory superelastic alloy so that the solid-state phase transformations can be designed to dictate the constrained delivery and unconstrained deployed diameters of the tip. The tip braid 220 can be trimmed to follow the contours of the reinforcing ring 211 and the ring can be welded or brazed over the ends of braid wires such that the tip section is pulled open into a funnel shape when allowed to expand. The reinforcing ring 211 can be heat set to a free shape with a larger expanded inner diameter 230 when the catheter 100 is deployed from the outer sheath. When collapsed, the reinforcing ring 211 and tip braid 220 can have an inner diameter approximate that of the catheter bore when constrained. Alternately, the wires of the braid can also be drawn filled tubing (DFT) shape memory alloy with a platinum core such that the braid is visible under fluoroscopy.

A further benefit of using a superelastic material for the braid wires and using the reinforcing ring as the primary structural support element for the tip section 210 is that the catheter walls can be relatively thinner without sacrificing performance characteristics such as flexibility or crush strength, adding robustness to tortuous bends for the tip section 210. The thinner walls allow a larger effective bore size for aspiration.

Radiopaque marker bands can be included at different axial points along the length of the catheter 100 for visibility under fluoroscopy during a procedure. In the example illustrated, a marker band 116 can illuminate the location of the distal end 114 of the shaft 110 to give an attending physician an indication of where the expandable capacity of the catheter begins. The band shown can be platinum strip or other noble metal with a relatively short length of between approximately 0.025-0.030 inches and a thin wall thickness (approximately 0.0005 inches) to minimize the impact on flexibility and the outer diameter of the catheter.

Figure 7:
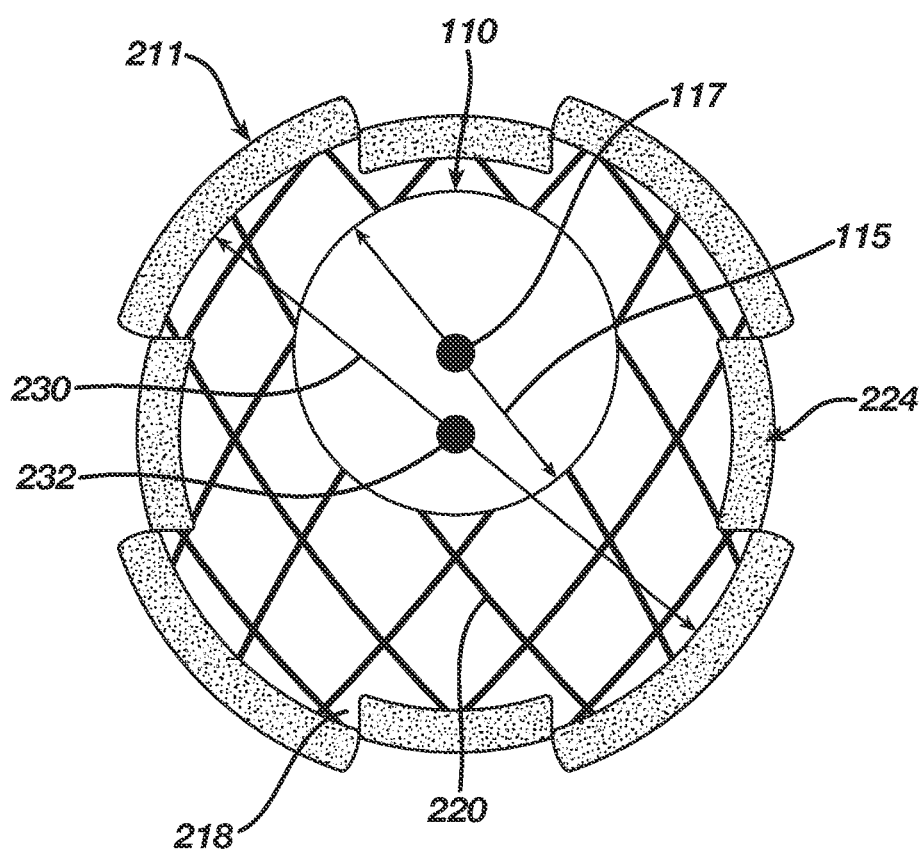
FIG. 7 is an end on view of the tip section of FIG. 6 according to aspects of the present invention.
Figure 8:
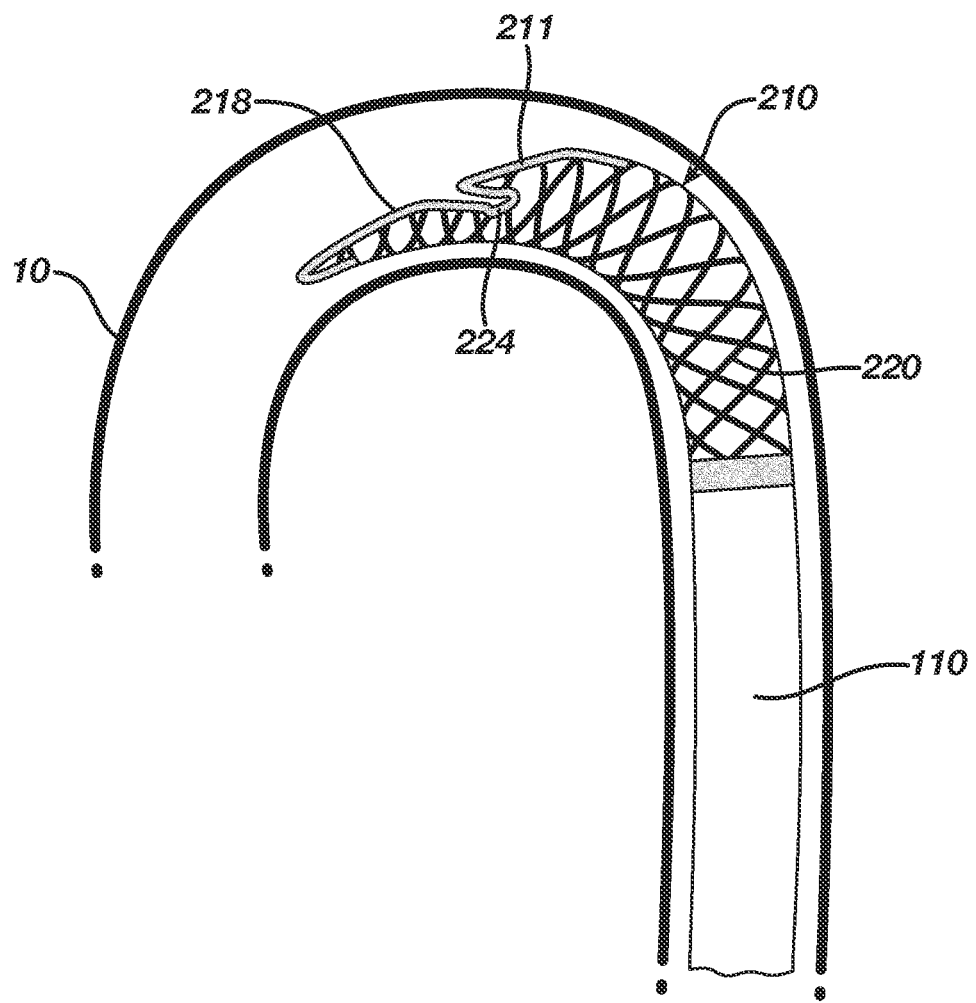
FIG. 8 is a view of a catheter being advanced through a bend in the vasculature according to aspects of the present invention.

As FIG. 6 and FIG. 7 show, when the tip section 210 is expanded the central axis and a large portion of the tip can be offset from the nominal longitudinal axis 111 of the shaft 110. The center 232 of the tip section can thus migrate radially away from being coincident with the shaft center 117 to become more asymmetric as the tip expands. Having an offset shape, and an oblique distal mouth 218, can increase lateral flexibility so the tip section 210 can better track and deflect of vessel walls when being advanced to a target site. FIG. 8 shows the beveled shape of the tip section 210 being able to deflect away from a tight bend when tracking in the vasculature 10, with the proximally extending cutouts of the relief features 224 allowing the tip section to respond and flex in the presence of localized forces. In many situations, when at a target site the catheter can also be manipulated and torqued so that the beveled mouth 218 of the tip section 210 is in-plane with the clot face, providing an increased access area for better clot management at the interface.

The expandable tip section 210 can be designed to be advanced through the vasculature in the expanded state. In these examples, the expandable tip can have a maximum inner diameter in the expanded state approximately equal to the diameter of a target vessel just proximal of the target clot. In most examples, the expanded funnel tip can be sized to have a larger inner diameter than the inner diameter of an outer sheath and/or guide through which it is delivered.

During delivery, the collapsed inner diameter 215 of the tip section can be approximately the same as the nominal diameter 115 of the catheter shaft section. When expanded, the expanded inner diameter 230 of the tip section 210 can be scaled linearly with the nominal diameter 115 of for the vessels to be accessed. For example, a catheter with an inner diameter of approximately 0.070 inches in the shaft can have a tip section 210 with a maximum inner diameter 230 of approximately 0.090 inches in the expanded deployed configuration. Similarly, catheters with shafts in other common sizes, such as 5 Fr up to 9 Fr, can also be envisioned with flared tip diameters 230 which scale accordingly, for an overall range of approximately 0.075-0.200 inches.

Figure 9:
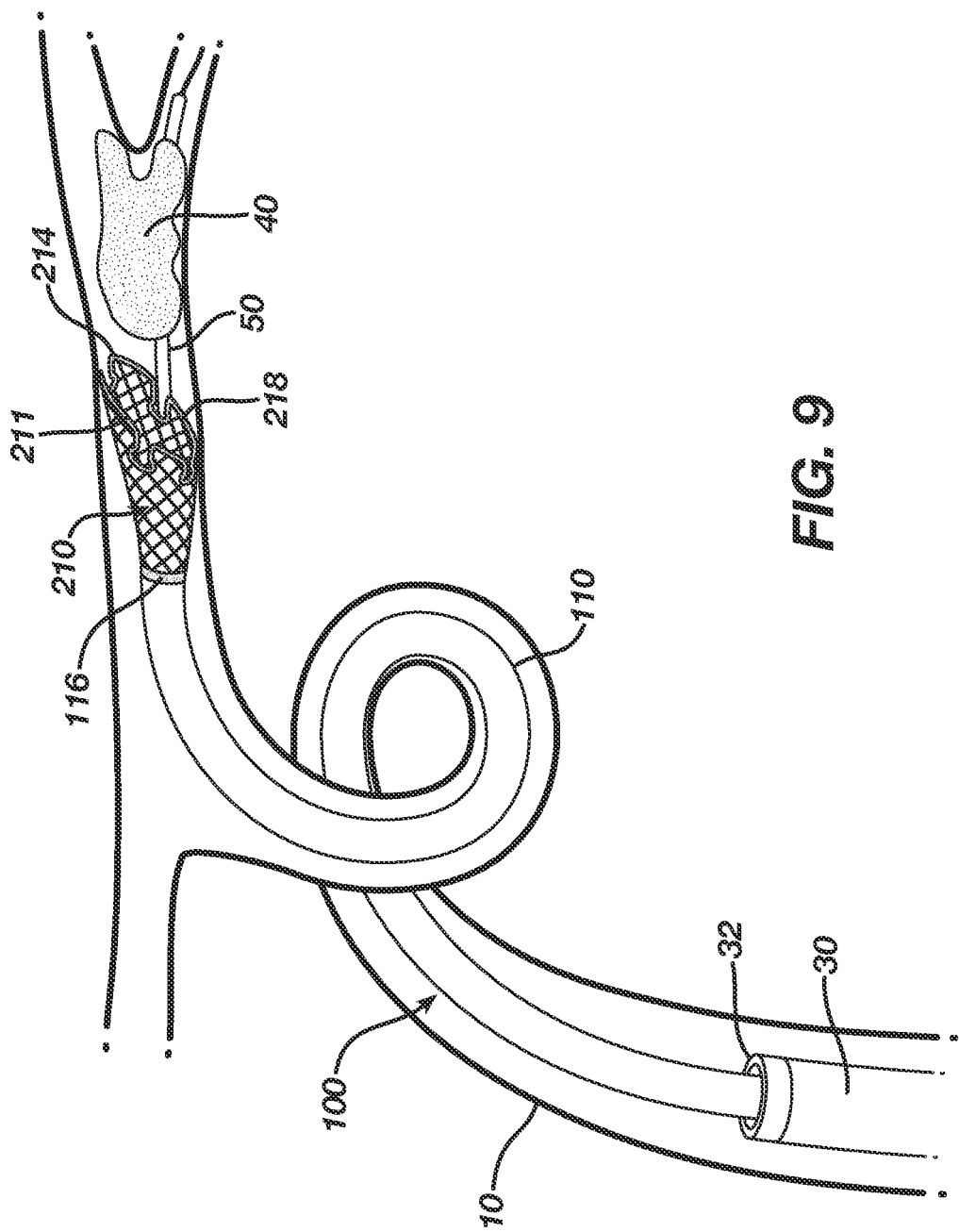
FIG. 9 illustrates a catheter deployed at a target site according to aspects of the present invention.

When using a catheter 100 of the present disclosure to clear an occlusion from a body vessel, the catheter with the tip collapsed can be advanced through an outer catheter or sheath 30 to a location proximal of a vessel occlusion, as depicted in FIG. 9. The sheath 30 is typically placed as close to the occlusive clot as practical, but the location can depend on the destination vessel size and the relative tortuosity of the vasculature needed to reach it. For example, in the case of a middle cerebral artery occlusion, the outer catheter might be placed in the internal carotid artery proximal of the carotid siphon. If for example the target occlusion is in an M1 vessel, a typical guide or outer sheath will need to be maintained in a position well proximal of these vessel diameters and the aspiration catheter 100 advanced independently.

As illustrated, the guide sheath 30 can be parked well upstream of the occlusive clot, and the catheter 100 advanced from the distal end 32 of the guide sheath to deploy to the expanded state. If pure aspiration proves insufficient to dislodge a clot, a microcatheter 50 can be used to deploy a stentriever or other devices known in the art. The combined stentriever and efficient aspiration through the enlarged bevelled tip section can act together to increase the likelihood of first pass success in removing a clot 40.

Once the clot has been dislodged from the vessel walls it can be progressively compressed through the funnel-shape of the expandable tip of the catheter and through the lumen into a canister or syringe. As the reinforcing ring provides support against collapse of the tip, a more flexible braid can be used to allow for additional localized radial expansion. Instead of the stentriever being withdrawn through the stationary lumen, the catheter 100 can also direct the aspiration vacuum to the clot face while being withdrawn in tandem with the stentriever so that a composite clot (comprised of friable regions and fibrin rich regions) is held together to prevent embolization. For a particularly firm clot, this additional expansion of the tip section can protect and shelter a lodged clot while the catheter itself is withdrawn.

Contrast can be injected to determine the extent to which the vessel is patent. Clot retrieval devices may be rinsed in saline and gently cleaned before being reloaded into the microcatheter for additional passes, if required.

Figure 10:
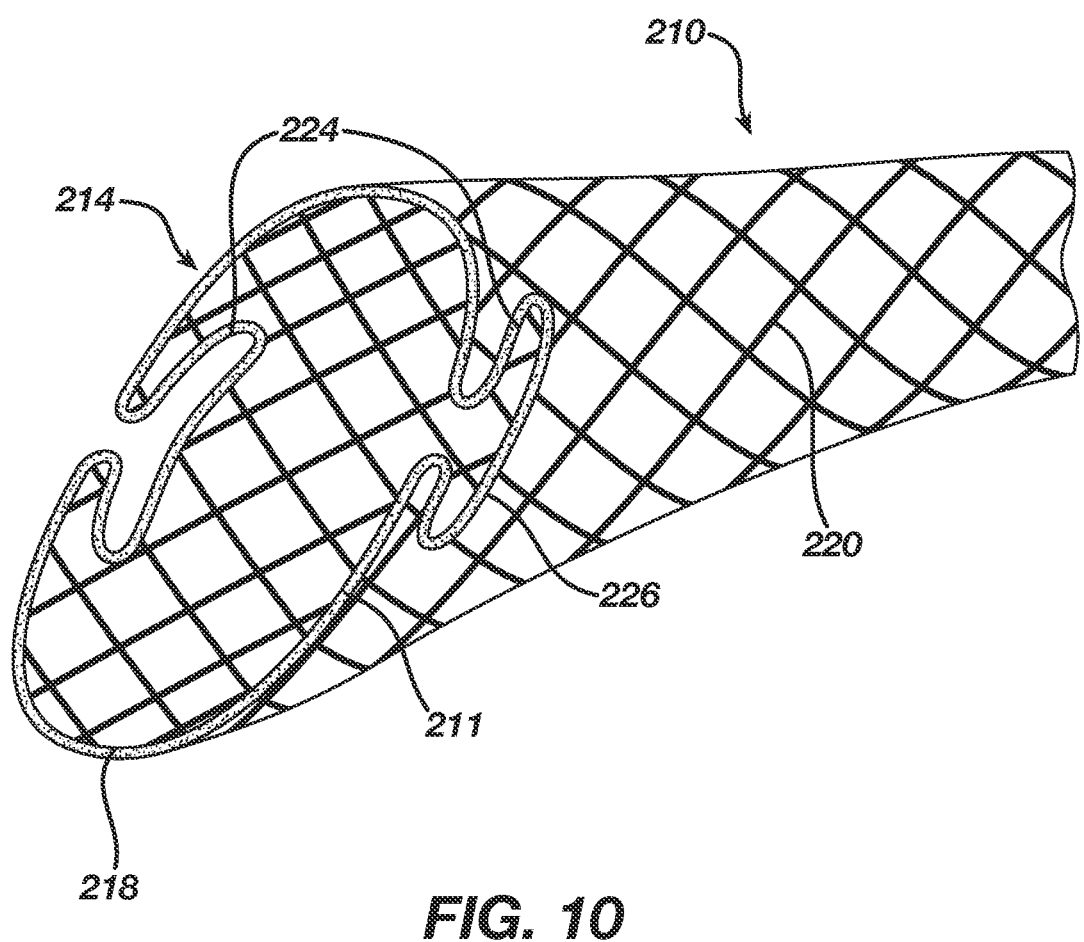
FIG. 10 is a view of another example of the distal portion of a clot retrieval catheter according to aspects of the present invention.

Another alternative design for the distal tip section 210 of the catheter according to the present disclosure is illustrated in FIG. 10. The beveled mouth 218 is determined by the perimeter of a reinforcing ring 211 having two relief features 224 spaced 180 degrees apart having exaggerated rounded sections 226. The relief features 224 can extend proximally from the mouth 218 such that at least a portion is offset from the angled plane of the bevel. A lesser number of relief features can increase the overall stiffness and available hoop strength of the reinforcing ring 211. This allows the ring to be used with a tip braid 220 of less density, offering a greater capacity for expansion.

Further, a configuration having two relief features 211 diametrically opposed as shown defines a bending plane for the tip section 210 passing through the two features. Alternately, additional relief features can be incorporated, including other geometric shapes that define additional planes.

The wires of the braid 220 of the tip section 210 can be cut and trimmed to the desired contours of the reinforcing ring 211 around the distal mouth 218. In this way the braid can resemble the end of a stent with free ends for greater flexibility and ease of manufacture. Alternatively, the wires of the underlying braid can be wound in one direction towards the distal end 214 of the tip section. Upon reaching a distal terminus, the wires can be inverted and wound proximally in the opposite direction. As a result, the inverted ends are also more atraumatic for additional manufacturing cost. In this example, the inverted ends of the braid can also be wrapped around the reinforcing ring 211 to improve the strength of the joint.

Figure 11:
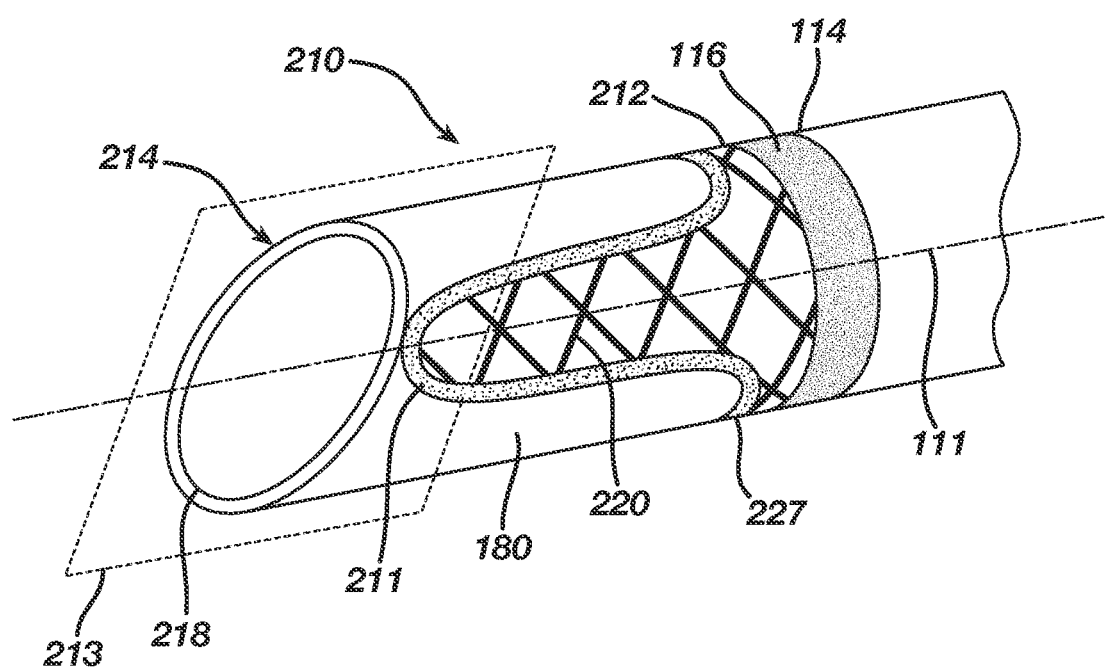
FIG. 11 depicts another example of the distal portion of a clot retrieval catheter according to aspects of the present invention.

FIG. 11 illustrates a design for the distal tip section 210 of the catheter where the reinforcing ring 211 has relief features 224 in the form of a series of axial slots 227 symmetric about the longitudinal axis 111. The axial slots 227 can be wide arcing loops extending proximally toward the marker band 116 from the beveled mouth plane 213 and enclose the tip braid 220 therein. Although there are many cases where the axial slots 227 or other relief features can substantially parallel the longitudinal axis 111, in other examples they can have parallel sections or a slot centerline which is angled or in a helix with respect to the axis. The use of a slot for the relief features can offer a more simplified manufacturing process compared to keyholes or other irregular geometric options.

The distalmost tip jacket 180 can be trimmed to follow the contours of the reinforcing ring 211 and relief features or can extend a longitudinal distance distally to overhang beyond the distal end of the ring. In the example shown in FIG. 11, the tip jacket extends beyond the perimeter of the reinforcing ring 211 in the regions of the axial slots 227 to yield a planar surface for the bevelled mouth 218 at the distal end 214 of the tip section 210. In some examples, the longitudinal distance of the overhang can be in a range from approximately 0.1 mm to approximately 1.0 mm. In a more specific example, this longitudinal distance can be in a range between 0.5 mm to approximately 0.8 mm.

The tip jacket 180 can also be the softest of the jackets used on the catheter and can cover approximately the distal 90 mm of the length. The additional integrity provided by the reinforcing ring 211 allows increasingly soft jacket materials to be implemented. Generally, a hardness in a range between approximately 42 Shore A to approximately 72 Shore A can be preferred. In one more specific example, a Neusoft jacket with a hardness of approximately 62 Shore A can be reflowed to form the tip jacket 180. In another case, an even softer Neusoft layer of approximately 42 Shore A can be used.

Figure 12A:
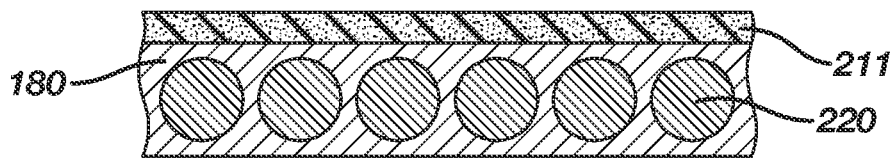
FIGS. 12a-12c shows ways in which the reinforcing ring and tip jacket can be oriented according to aspects of the present invention.
Figure 12B:
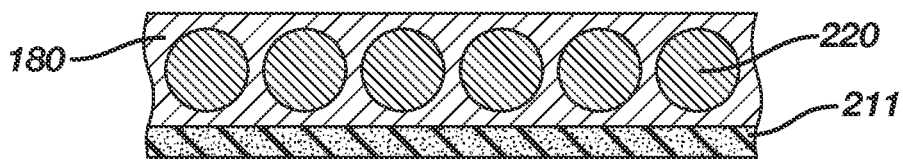
Figure 12C:
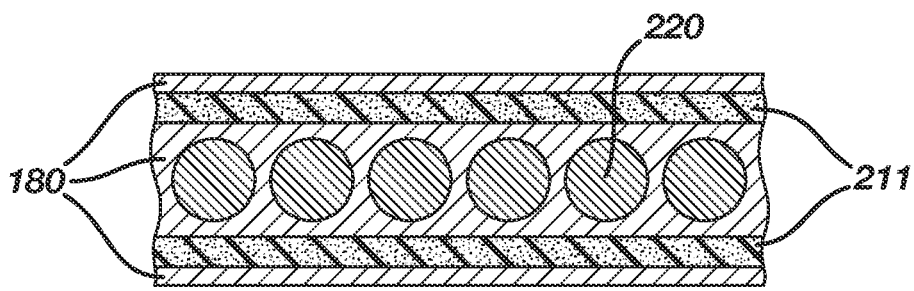

Cross sections demonstrating various examples of the layered layout of the reinforcing ring 211, tip jacket 180, and tip braids 220 of the distal tip section 210 are shown in FIGS. 12a-c. The jacket 180 can be applied and adhered to the braid and ring through dip coating, reflow, lamination, or other suitable method. In the example shown in FIG. 12a, the reinforcing ring 211 structure runs radially outside and over of the braid 220, which is encapsulated by the tip jacket 180. This layout enables the reinforcing ring to protect the distal jacket from abrasion or tearing, especially for instances when a softer, more fragile jacket is utilized. The edges of the reinforcing ring can have a radii or chamfer to protect the traversed vascular beds.

The alterative shown in FIG. 12b can be used for when a slightly harder, more durable material is chosen for the jacket. The jacket-encased braid 220 can be positioned radially outboard and adhered to the exterior surface of the reinforcing ring 211. In this configuration, the reinforcing ring is used to "push" the braid and jacket material outward as the tip section 210 is expanded. Similarly, the reinforcing ring will "pull" the braid and jacket material inward as the tip section is collapsed into an outer sheath.

In a further example, an arrangement where the braid 220 is sandwiched by the reinforcing ring 211 and the outer tip jacket 180 completely encapsulates both the braid wires and reinforcing ring is portrayed in FIG. 12c. To form this construction, a thin inner jacket layer can be disposed on a flared mandrel and the mandrel loaded proximally into the distal end of the braid/reinforcing ring combination to radially expand the tip section. A thin elastic outer polymer layer of the tip jacket extrusion can be threaded or stretched over the flared mandrel and pushed over the flared section to expand the undersized material of the extrusion. The combined inner and outer layers of the tip jacket 180 can then be reflowed in place and the flared mandrel removed from the catheter assembly.

With a sandwiched braid and the jacket material encasing all of the underlying assembly, the configuration in FIG. 12c can offer the most uniform "push" and "pull" forces acting on the tip section. Additionally, a fully-homogenous jacket edge is formed at the distal end 214 of the tip section 210.

The invention is not necessarily limited to the examples described, which can be varied in construction and detail. The terms "distal" and "proximal" are used throughout the preceding description and are meant to refer to a positions and directions relative to a treating physician. As such, "distal" or "distally" refer to a position distant to or a direction away from the physician. Similarly, "proximal" or "proximally" refer to a position near or a direction towards the physician. Furthermore, the singular forms "a," "an," and "the" include plural referents unless the context clearly dictates otherwise.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g., "about 90%" may refer to the range of values from 71% to 99%.

In describing example embodiments, terminology has been resorted to for the sake of clarity. As a result, not all possible combinations have been listed, and such variants are often apparent to those of skill in the art and are intended to be within the scope of the claims which follow. It is intended that each term contemplates its broadest meaning as understood by those skilled in the art and includes all technical equivalents that operate in a similar manner to accomplish a similar purpose without departing from the scope and spirit of the invention. It is also to be understood that the mention of one or more steps of a method does not preclude the presence of additional method steps or intervening method steps between those steps expressly identified. Similarly, some steps of a method can be performed in a different order than those described herein without departing from the scope of the disclosed technology.

What is claimed is:

1. A catheter comprising:
   a proximal elongate shaft comprising a longitudinal axis, a distal end, a lumen, and a shaft braid; and
   an expandable distal tip section at the distal end of the elongate shaft, the expandable distal tip section comprising a collapsed delivery configuration, an expanded deployed configuration, a tip braid, and a distal mouth comprising a beveled profile and a perimeter defined by a reinforcing ring;

wherein the reinforcing ring comprises a plurality of relief features spaced equally around the longitudinal axis, and wherein a proximal end of the tip braid is attached to a distal end of the shaft braid.

2. The catheter of claim 1, the expandable distal tip section further comprising a substantially circular cross section in both the collapsed delivery configuration and expanded deployed configuration.

3. The catheter of claim 1, wherein the reinforcing ring is welded to the tip braid of the expandable distal tip section.

4. The catheter of claim 1, wherein the reinforcing ring is overmolded to the tip braid of the expandable distal tip section.

5. The catheter of claim 1, wherein the reinforcing ring comprises a shape memory alloy.

6. The catheter of claim 5, wherein the reinforcing ring is heat set to comprise an expanded inner diameter larger than a collapsed inner diameter when the distal tip section is in the expanded deployed configuration.

7. The catheter of claim 1, wherein at least a portion of the tip braid is heat set to comprise an expanded inner diameter larger than a collapsed inner diameter when the expandable distal tip section is in the expanded deployed configuration.

8. The catheter of claim 1, wherein the reinforcing ring comprises a polymeric composition.

9. The catheter of claim 1, wherein the tip braid is cut to follow the contours of the relief features at the distal end of the expandable distal tip section.

10. The catheter of claim 1, wherein the distal mouth defines a plane passing through at least a portion of the reinforcing ring, the plane forming an acute angle with respect to the longitudinal axis when the expandable distal tip section is in the collapsed delivery configuration.

11. The catheter of claim 10, wherein the angle is between approximately 30 degrees and approximately 60 degrees.

12. The catheter of claim 10, wherein at least a portion of the relief features of the reinforcing ring is located offset proximally from the plane.

13. The catheter of claim 1, wherein the relief features reduce the cross sectional profile of at least a portion of the expandable distal tip section.

14. The catheter of claim 1, wherein the relief features comprise a keyhole shape having a parallel section and a rounded section.

15. The catheter of claim 1, wherein the relief features comprise axial slots extending proximally from the distal perimeter of the distal mouth.

16. A catheter comprising:
a proximal elongate shaft comprising a longitudinal axis, a distal end, a lumen, a shaft braid, and a marker band at the distal end of the shaft;
an expandable distal tip section connected to the distal end of the elongate shaft, the expandable distal tip section comprising a collapsed delivery configuration, an expanded deployed configuration, a supporting tip braid, and a reinforcing ring attached to the distal end of the tip braid; and
a polymer tip jacket disposed around the expandable distal tip section;
wherein at least a portion of the reinforcing ring defines a mouth plane forming an acute angle with respect to the longitudinal axis when the expandable distal tip section is in the collapsed delivery configuration;
wherein the reinforcing ring comprising a plurality of relief features spaced equally around the longitudinal axis, at least a portion of each of the relief features being proximally offset from the mouth plane, and
wherein a proximal end of the tip braid is attached to a distal end of the shaft braid.

17. The catheter of claim 16, wherein the distal edge of the polymer tip jacket follow the contours of the reinforcing ring.

18. The catheter of claim 16, wherein at least a portion of the polymer tip jacket extend distally beyond the contours of the reinforcing ring.

19. The catheter of claim 16, wherein the polymer tip jacket has a hardness in a range between approximately 42 Shore A to approximately 72 Shore A.

20. The catheter of claim 16, wherein in the expanded deployed configuration, a circular profile of the expandable distal tip section has a center radially offset from the longitudinal axis of the elongate body.

* * * * *